US012766024B2

(12) United States Patent
Bruckmann

(10) Patent No.: US 12,766,024 B2
(45) Date of Patent: Oct. 20, 2026

(54) MOBILIZING MUSCULOSKELETAL STRUCTURES

(71) Applicant: J.W. Barry Bruckmann, Nassau (BS)

(72) Inventor: J.W. Barry Bruckmann, Nassau (BS)

( * ) Notice: Subject to any disclaimer, the term of this patent is extended or adjusted under 35 U.S.C. 154(b) by 0 days.

(21) Appl. No.: 18/764,960

(22) Filed: Jul. 5, 2024

(65) Prior Publication Data

US 2024/0358538 A1 Oct. 31, 2024

Related U.S. Application Data

(63) Continuation of application No. 16/994,638, filed on Aug. 16, 2020, now Pat. No. 12,059,367, which is a continuation of application No. 14/214,521, filed on Mar. 14, 2014, now abandoned.

(60) Provisional application No. 61/798,388, filed on Mar. 15, 2013.

(51) Int. Cl.
*A61F 5/01* (2006.01)

(52) U.S. Cl.
CPC ............ *A61F 5/013* (2013.01); *A61F 5/0111* (2013.01); *A61F 5/0118* (2013.01); *A61F 5/019* (2013.01)

(58) Field of Classification Search
CPC ...... A61F 5/05875; A61F 5/0118; A61F 5/10; A61F 2013/00093; A61F 5/05866; A61F 13/10; A61F 13/105; A61F 2/7812; A41D 13/082; A41D 19/01588
USPC ...................... 602/12, 22, 63; 128/880; 2/21
See application file for complete search history.

(56) References Cited

U.S. PATENT DOCUMENTS

| | | | | |
|---|---|---|---|---|
| 4,813,406 | A * | 3/1989 | Ogle, II | A61F 5/05875 602/30 |
| 5,101,812 | A * | 4/1992 | Wang | A61F 5/0113 128/880 |
| 12,059,367 | B2 * | 8/2024 | Bruckmann | A61F 5/0118 |
| 2009/0301497 | A1 * | 12/2009 | Bruckmann | A43B 7/00 602/5 |

* cited by examiner

*Primary Examiner* — Caitlin A Carreiro
(74) *Attorney, Agent, or Firm* — AdamsIP, LLC

(57) ABSTRACT

A device for enclosing a finger includes a protective shell having an opening for receiving the finger. The protective shell defines an interior cavity that is sized and shaped to allow extension and flexion of the finger within the shell.

10 Claims, 26 Drawing Sheets

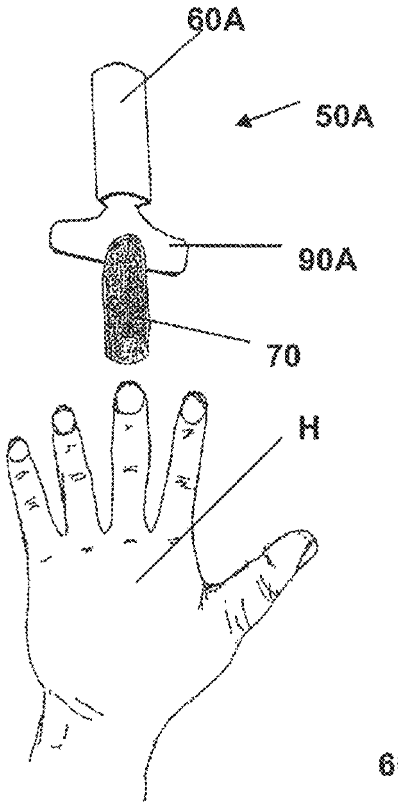
FIG. 9
FIG. 9A
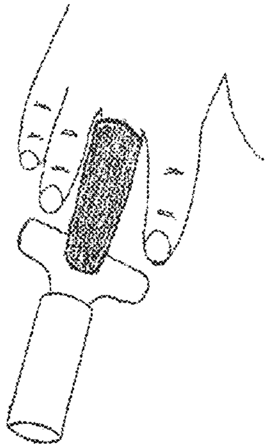
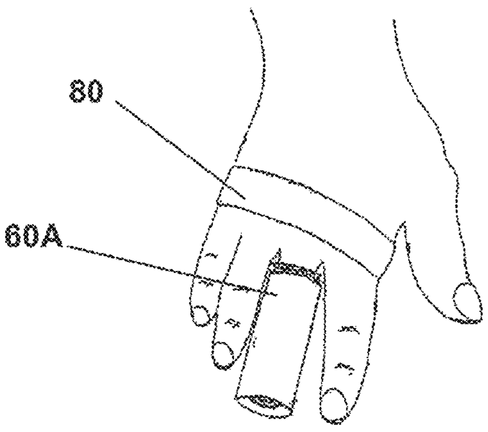
FIG. 9B

MOBILIZING MUSCULOSKELETAL STRUCTURES

CROSS-REFERENCE TO RELATED APPLICATIONS

This application is a continuation of U.S. application Ser. No. 16/994,638, filed Aug. 16, 2020, which is a continuation of U.S. application Ser. No. 14/214,521, filed Mar. 14, 2014, which claims priority to U.S. Provisional application No. 61/798,388, filed Mar. 15, 2013, which applications are incorporated by reference herein in their entirety.

TECHNICAL FIELD

This disclosure relates to mobilizing musculoskeletal structures, including injured musculoskeletal structures.

BACKGROUND

Casts, splints, bandages, and braces are used to stabilize, immobilize, or otherwise protect or support, musculoskeletal disorders such as traumatic injuries, e.g., fractures, deformities, and other problems of bones, joints, and connective tissues of the body ("injury sites"). Protecting and sup-porting the injury site can assist in reducing pain or discom-fort, reducing inflammation, providing physical support, promoting healing, and protecting from further damage or injury. Supporting and protecting an injury site typically involves immobilizing the injury site. For example, one treatment for fractures of the bones of the toes (the phalanges) includes taping the injured toe to an adjacent toe to limit independent movement of the injured toe. Additionally or alternatively, a splint is sometimes attached to an injured toe in an attempt to immobilize and protect the injured toe.

SUMMARY

An injured musculoskeletal structure, such as a broken toe or finger bone, is also susceptible to painful and potentially damaging forces. Particularly, normal use of interconnected musculoskeletal structures can transfer forces to the injury site, potentially causing pain and inflammation, and potentially hindering healing of the injury. For example, when a person steps down on the foot, the metatarsals normally move down and forward in relation to the heel, and they also spread to the sides in relation to one another. Thus, mobilizing an injured musculoskeletal structure relative to a support device can allow natural movement of the injured musculoskeletal structure, and can reduce undesired transfer of forces to the injured musculoskeletal structure during healing.

According to one aspect, a device includes a protective shell having an opening for receiving the finger. The protective shell defines an interior cavity sized and shaped to allow extension and flexion of the finger within the shell. Implementations of this aspect may include one or more of the following features. For example, the protective shell may be not attached to the enclosed finger but may be attached to another part of a hand of the enclosed finger. The protective shell may further define an outer surface proximate the opening for supporting a base of the finger. The protective shell may include a pair of sidewalls that are substantially parallel to a sagittal plane of the hand. The pair of sidewalls may be spaced apart from each other to provide clearance space on one or both sides of the finger. The pair of sidewalls may be spaced apart from each other to limit lateral motion of the finger. A volar side of the protective shell may have an arcuate shape. The arcuate shape may correspond to a partial or substantially full range of motion of the finger. The interior cavity may have a generally semi-cylindrical volume. The interior cavity may be sized and shaped to allow partial or full extension and flexion of the finger. The interior cavity may be sized and shaped to accommodate a finger with a splint, bandage, or other devices configured to support or protect all or a part of the finger. The interior cavity may include a slippery inner surface configured to provide a low friction interface between the protective shell and the finger, splinted finger, or bandaged finger. The shell may be adjustable, or have adjustable components, to provide varying limitations of flexion or extension of a finger. The protective shell may be rigid.

The device may further include an interface member positionable between the finger and an inner surface of the protective shell. The interface member may be configured to be placed on the finger prior to inserting the finger into the protective shell. The interface member may be in the shape of a sock. A splint, bandage, or other protective device attached to a finger may serve as an interface member or may be combined with the use of an interface member.

The protective shell may include a dorsal tab that protrudes proximally from a dorsal side of the opening. The dorsal tab may be configured to contact a dorsal side of the hand. The dorsal tab may be shaped to conform to a knuckle of the finger. The dorsal tab may define an opening configured to receive and retain a portion of an open end of an interface member, with the interface member being positionable between the finger and an inner surface of the protective shell. The dorsal tab may be all or partly rigid, semi-rigid, or flexible. The open end portion of the interface member may be, or may be shaped as, a rolled edge. The protective shell may define slots for receiving an attachment device for attaching the protective shell to a musculoskeletal structure of the hand or arm. The device may further include an attachment device for attaching the protective shell to the musculoskeletal structure of the hand or arm, the attachment device including at least one of a tab, a tape, a strap, a tie, a clip, and a hook-and-loop fastener. The protective shell may define one or more ventilation openings.

The device may further include one or more laterally protruding stabilizing tabs that may be configured for receiving an attachment device for attaching the protective shell to a musculoskeletal structure of the hand or arm. The stabilizing tabs may be configured to contact a palm of the hand. The stabilizing tabs may protrude laterally outward from slots defined in the protective shell. The stabilizing tabs may be sized and shaped to be adjustable in length, and to slide and move within a slot to allow for angulation and positioning of the protective shell to align the shell with normal or desired finger movement. The stabilizing tabs may be all or partly rigid, semi-rigid, or flexible.

According to another aspect, a device for enclosing a finger includes a protective shell for receiving the finger. The protective shell is sized and shaped to provide clearance space around a circumference of the finger. The protective shell includes a tubular portion. The protective shell also includes an end cap portion configured to be removably coupled to a distal end of the tubular portion and enclose a distal tip of the finger.

Implementations of this aspect may include one or more of the following features. For example, the protective shell may be attached to a part of the hand or arm without being attached to the enclosed finger. The end cap portion may be made and supplied in varying lengths to provide a kit for accommodating fingers of different lengths. The tubular portion may be configured to juxtapose two or more phalanges of the finger. An outer surface of the protective shell may include one or more hooking elements configured to secure an open end portion of an interface member positionable between the finger and an inner surface of the protective shell. The device may further include an interface member positionable between the finger and an inner surface of the protective shell. The device may further include a tab or knuckle guard that may be configured to couple to a dorsal side of the protective shell and extend proximally beyond a proximal end of the tubular portion. The tab or knuckle guard may be all or partly rigid, semi-rigid or flexible. The tubular portion may be substantially cylindrical in shape or may be substantially rectangular in shape. The tubular portion may be curved along a length of the tubular portion. The protective shell may be all or partly rigid, flexible or semi-rigid. The protective shell may define one or more ventilation openings. The end cap may define one or more ventilation openings. The coupling between the end cap portion and the tubular portion may be a snap-fit, an interference-fit, or a screw-fit.

In one general aspect, a device includes a shell member sized and shaped to juxtapose an injured digit of a limb during healing. The shell member has a digit-facing surface formed of a slippery material to mobilize the injured digit relative to the shell member. The device also includes means for limiting movement of the shell member relative to an adjacent healthy musculoskeletal structure of the limb.

Some implementations may include one or more of the following features. The device includes an interface member disposed between the injured digit and the shell member to facilitate movement of the injured digit relative to the shell member. The means for limiting movement of the shell member relative to an adjacent healthy musculoskeletal structure includes a slip-resistant body-facing surface juxtaposing the adjacent healthy musculoskeletal structure of the limb. The means for limiting movement of the shell member relative to an adjacent healthy musculoskeletal structure includes a hook-and-loop fastener.

The shell member is formed as a shoe insole. The device includes an upstanding deflection member configured to at least partially cover an injured toe. The digit-facing surface includes an upper surface portion of the shell member on which a wearer's foot rests during use, and the means for limiting movement includes an upper surface portion of the shell member on which the wearer's heel or instep rests during use. The shell member defines a space in which the wearer's heel does not rest on the shell during use, and the means for limiting movement of the shell member relative to an adjacent healthy musculoskeletal structure of the limb includes the space.

The device includes an interface member formed as a sock configured to cover a wearer's foot, and the sock is configured for sliding engagement with the digit-facing surface and substantially non-sliding engagement with the upper surface portion of the shell member on which the wearer's heel or instep rests.

The shell member defines an interior cavity configured to receive at least a portion of the injured digit, and the digit-facing surface includes an inner surface of the shell member. The device further includes an interface member including a splint or a sleeve. The device includes a deflection member configured to at least partially enclose the injured digit to protect the injured digit from damaging contact.

The device includes a shoe member that is configured to receive the shell member. The shoe member includes the means for limiting movement of the shell member relative to an adjacent healthy musculoskeletal structure of the limb.

In another general aspect, a splint for supporting an injured musculoskeletal structure includes a rigid supportive shell configured to cradle an injured musculoskeletal structure. The supportive shell limits bending of the injured musculoskeletal structure in a first direction. An interface member is disposed between a portion of a wearer's body and at least a portion of the supportive shell to mobilize at least one of the injured musculoskeletal structure and a musculoskeletal structure adjacent to the injured musculoskeletal structure relative to the supportive shell.

In another general aspect, a process includes providing a device for mobilizing an injured musculoskeletal structure to slide relative to an orthotic member juxtaposing the injured musculoskeletal structure to support the injured musculoskeletal structure during healing.

In another general aspect, supporting an injured musculoskeletal structure during healing includes mobilizing the injured musculoskeletal structure to slide relative to an orthotic member juxtaposing the injured musculoskeletal structure.

Some implementations may include one or more of the following features. Supporting an injured musculoskeletal structure includes isolating the injured musculoskeletal structure from the orthotic member such that the orthotic member limits the transfer of a force to the injured musculoskeletal structure when moving with a body portion to which the orthotic member is attached. The method includes retaining the orthotic member to a healthy musculoskeletal structure during use, substantially limiting bending of the injured musculoskeletal structure in a first direction, or at least partially enclosing the injured musculoskeletal structure to protect against damaging contact.

In another general aspect, supporting an injured musculoskeletal structure includes placing an interface member on an exterior skin surface juxtaposing the injured musculoskeletal structure and placing a shell member in a position juxtaposing the injured musculoskeletal structure. The interface member facilitates sliding movement of the injured musculoskeletal structure and/or an adjacent musculoskeletal structure relative to the shell member during support.

In another general aspect, a device includes a shell member sized and shaped to juxtapose an injured toe during healing. The shell member includes a first, foot-facing surface portion formed of a slippery material to mobilize the injured toe relative to the first surface portion, and a second, foot-facing surface portion having a higher coefficient of friction than the first surface portion and arranged relative to the first surface portion to support a healthy musculoskeletal structure adjacent the injured toe and to limit sliding between the second surface and the healthy musculoskeletal structure.

In another general aspect, a device includes a shell member sized and shaped to juxtapose a foot sole at a location proximate an injured toe while not juxtaposing adjacent portions of the sole. The shell member includes a foot-facing surface formed of a slippery material to mobilize the injured toe relative to the foot-facing surface.

In another general aspect, a device includes a shell member sized and shaped to juxtapose an injured finger or thumb during healing. The shell member includes a first digit-facing surface portion formed from a slippery material to mobilize the injured finger or thumb relative to the first surface portion and a second surface portion configured to immobilize the shell member relative to healthy musculoskeletal structure adjacent the injured finger or thumb.

In another general aspect, a device includes a shell member sized and shaped to juxtapose an injured metacarpal structure during healing. The shell member includes a first surface portion configured to immobilize the shell member relative to the injured metacarpal structure and a second digit-facing surface portion formed from a slippery material to mobilize a finger or thumb adjacent the injured metacarpal structure relative to the second surface portion.

In one general aspect, a device includes a shell member sized and shaped to juxtapose an injured musculoskeletal structure of a limb during healing. The shell member has a surface configured to face the injured musculoskeletal structure and/or an adjacent musculoskeletal structure. The surface is formed of a slippery material to mobilize the injured musculoskeletal structure and/or the adjacent musculoskeletal structure relative to the shell member. The device also includes means for limiting movement of the shell member relative to an adjacent healthy musculoskeletal structure of the limb.

In some implementations, musculoskeletal structures adjacent to an injured musculoskeletal structure are mobilized. For example, other bones, skeletal muscles, cartilage, and/or tendons in the forefoot, in addition to the injured musculoskeletal structure, can be mobilized relative to a support device to limit painful and/or injurious forces from being transferred to an injured toe during standing or walking. In other implementations, the musculoskeletal structures adjacent to, and/or adjoining an injured musculoskeletal structure are mobilized instead of the injured musculoskeletal structure. Additionally, the mobilized adjacent and/or adjoining musculoskeletal structures include those structures distal to the injured musculoskeletal structure. For example, a healthy toe can be mobilized relative to a support device to protect a connected metatarsal bone or joint such that when the metatarsal bone pushes forward or outward against the toe during walking, the mobilized toe moves with the internal motion of the connected metatarsal bone. Mobilizing the toe minimizes resistance against such internal movements of the metatarsal bone, and reducing painful and/or injurious forces transferred to the injury site.

The details of various implementations set forth in the accompanying drawings and description. Other features and advantages will be apparent from the description and drawings, and from the claims.

BRIEF DESCRIPTION OF THE DRAWINGS

FIG. 9 is an exploded view of another orthotic sup-port device.

FIGS. 9A and 9B are perspective views of the orthotic support device of FIG. 9.

Like reference symbols in the various drawings indicate like elements.

DETAILED DESCRIPTION

An injured musculoskeletal structure is mobilized relative to a juxtaposing support device by a low friction interface provided where the support device contacts the injury site. For example, as will be discussed in further detail below, in the case of a toe fracture the support device provides a slippery surface located on a surface facing the injured toe such that a very low friction interface is provided between the injured toe and the support device. This allows the injured toe to move relative to the support device when pressure is applied to the foot, e.g., when the patient stands or walks, causing the metatarsal bones to spread and push forward in relation to the heel of the foot and in relation to the support device. Because the toe can slide over the slippery surface to accommodate these movements of the musculoskeletal structure of the foot, pressure and stress on the toe are reduced, thereby reducing pain and inflammation, and reducing the likelihood of further damage to the injured toe.

Figure 1:
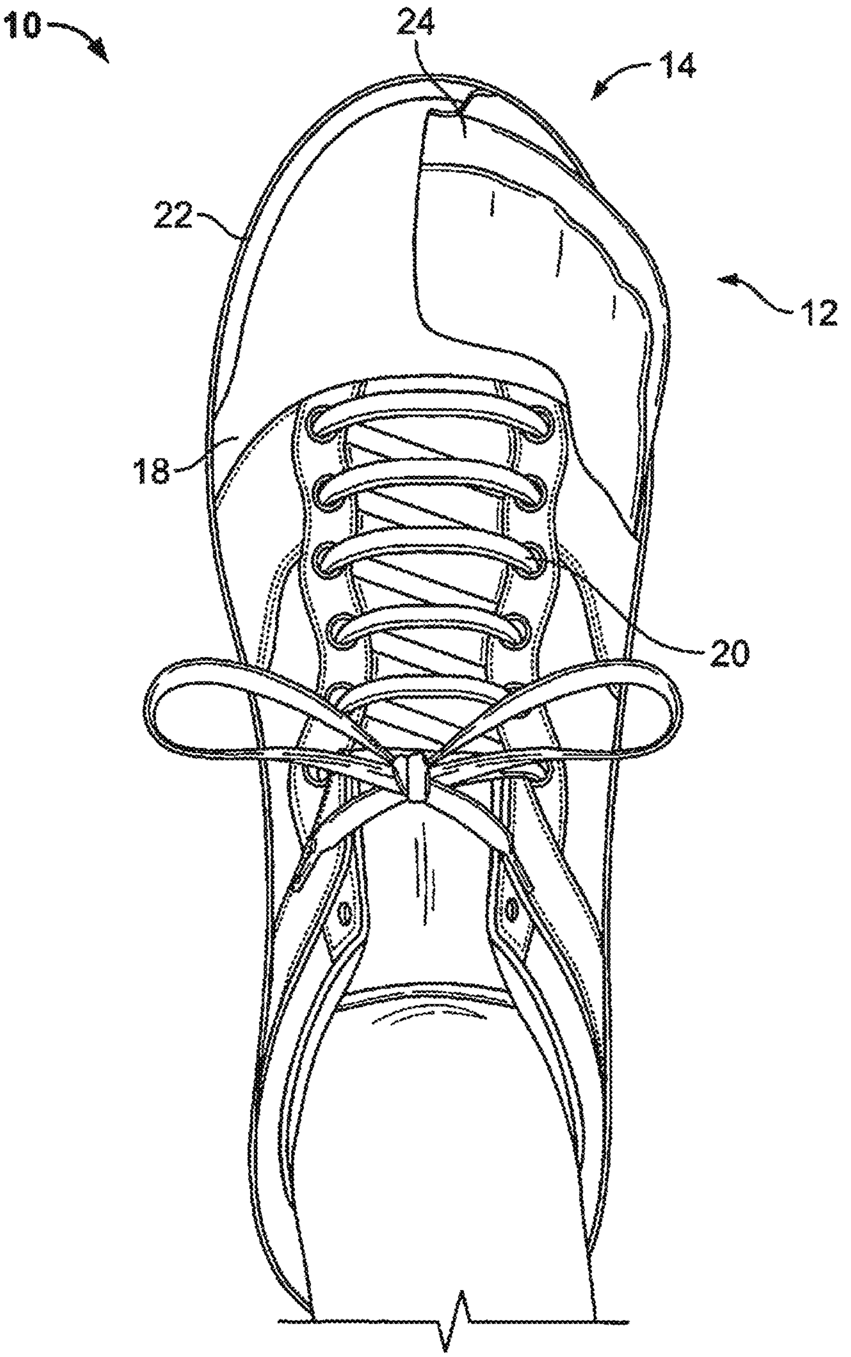
FIG. 1 is a top view of an orthotic support device according to one implementation.
Figure 2:
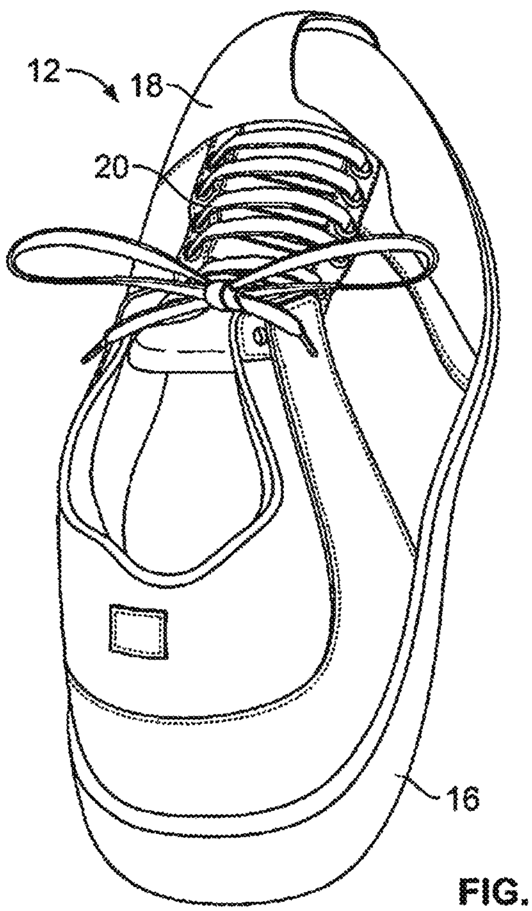
FIG. 2 is a perspective view of the orthotic support device shown in FIG. 1, with the low friction liner removed.
Figure 2A:
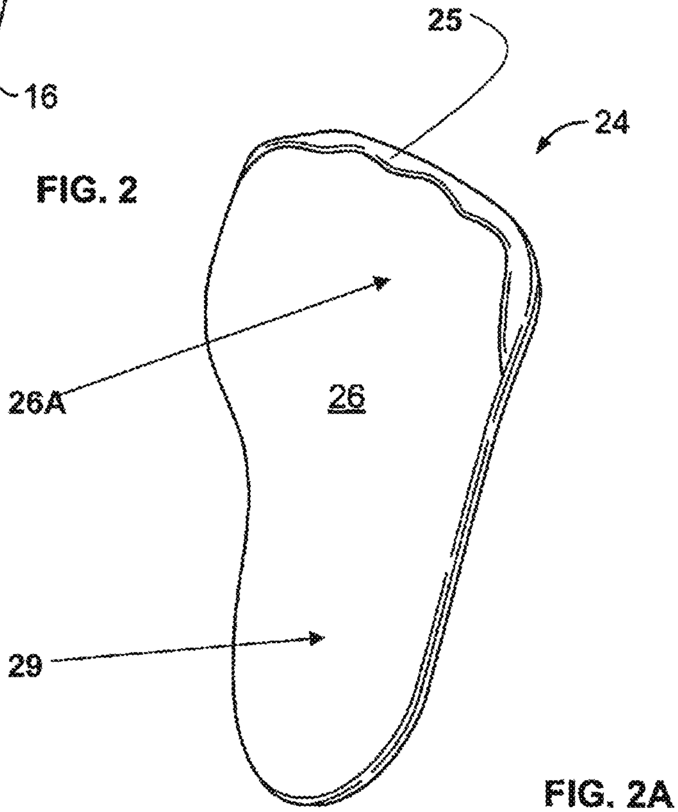
FIG. 2A is a plan view of the low friction liner of the orthotic support device shown in FIG. 1.
Figure 3:
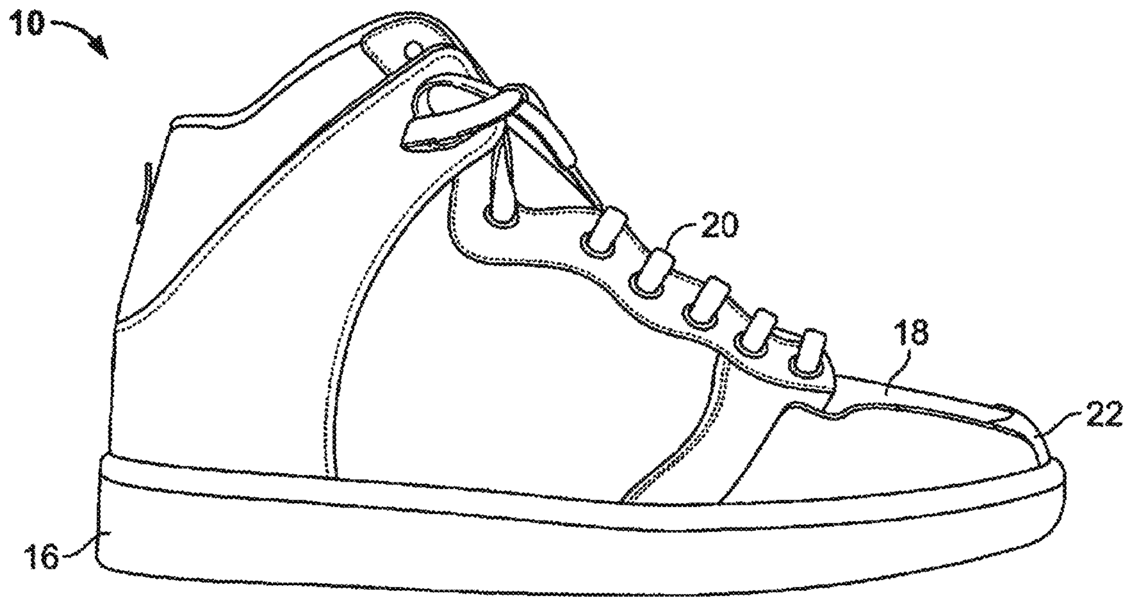
FIG. 3 is a side view of the orthotic support device shown in FIG. 1 with the low friction liner removed.

Referring to FIGS. 1-3, a mobilizing support device 10 for supporting an injured foot, e.g., having a toe fracture, a deformed toe, or other musculoskeletal injury, includes a shoe portion 12 having an open area 14 surrounding the injury site. The open area 14 is arranged such that contact between the injured musculoskeletal structure of the foot and the shoe portion 12 is reduced or eliminated. Thus, during walking or standing, the shoe portion 12 does not contact the top, end, or sides of the injured musculoskeletal structure. The shoe portion 12 includes a sole 16, an upper 18, a lacing system 20, and a toe cover 22 positioned adjacent the open area 14 to protect uninjured toes from impact with external objects.

Figure 5:
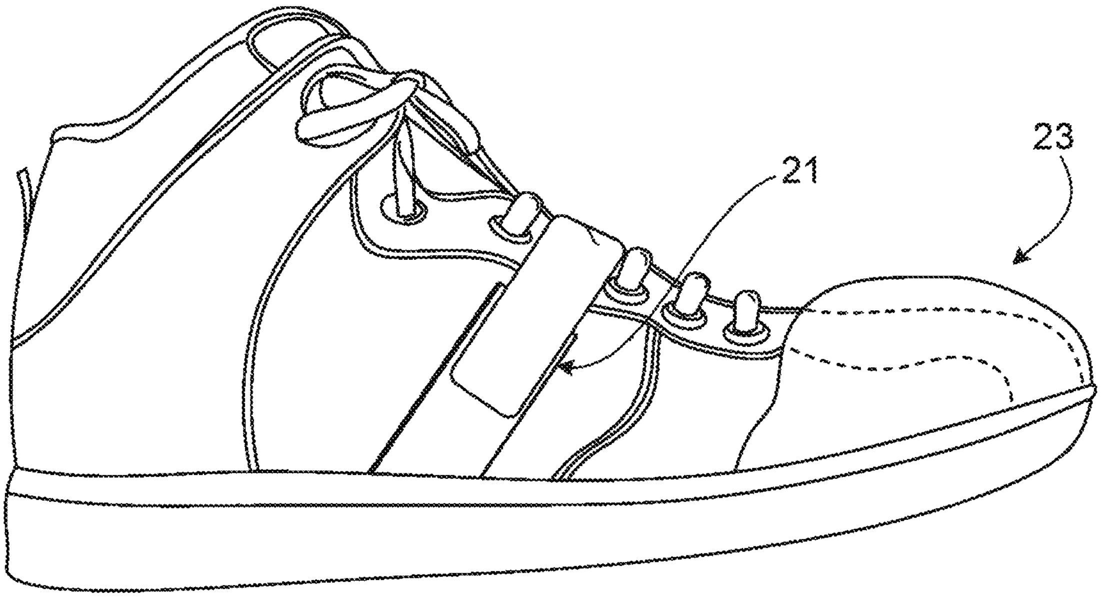
FIG. 5 is a side view of an orthotic support device in which an open area of the shoe portion of the device is replaced by an enlarged protective area.

In an alternative embodiment, shown in FIG. 5, the open area 14 and toe cover 22 are replaced, at least in part, by an enlarged, protective area 23. Protective area 23 has sufficient dimensions to provide clearance around the injured musculoskeletal structure. For example, the protective area 23 provides a clearance distance of from about 0.125" to about 1.0" around the top, end, and sides of the injured toe(s), and is formed of a material that is sufficiently stiff to provide a desired degree of protection to the toes from an impact from the front or above, e.g., an object being dropped on the foot. The protective area 23 can include perforations or other ventilation structure, and can be lined with a low friction material to provide a low friction sliding interface with the toes in case the toes contact the inner surface of the enlarged protective area 23. Ideally, the open area or enlarged area is configured to allow the injury site to slide relative to the insole, as will be discussed further below, without contact of the upper part of the injured area with the device 10.

The lacing system 20 holds in place a portion of the limb that is adjacent to the injury site, such as the heel, ankle, and/or calf, relative to the shoe portion 12 and allows adjustment of the size of the shoe, e.g., to accommodate swelling and to allow the wearer to easily don and remove the shoe. For example, the lacing system can retain musculoskeletal structures of the heel and/or ankle in generally slip-free communication with the upper 18. The lacing system can be replaced by, and/or supplemented with, any suitable attachment device, for example hook and loop fastener strips 21 such as those available commercially under the tradename Velcro®, or other adjustable straps. Snaps, clips, buckles, and other latching and/or cinching devices can also be used. In some implementations, the upper 18 extends over the ankle area, to provide additional support and immobilization of selected musculoskeletal structures of the foot relative to the shoe portion 12, For example, the upper 18 may be similar to that of a high top sneaker, a hiking shoe, or boot.

Referring to FIG. 2, a liner 24 is disposed inside the shoe 12, and functions both as an insole and as a low-friction sliding surface. As shown in FIG. 1, the liner 24 is sized such that it extends beyond the position of the toes when weight is carried by the foot, so that there is room for the toes to slide forward and outward when the wearer steps or stands on the foot. For example, the liner 24 extends horizontally a distance of approximately 0.25" or more beyond the perimeter of expected movements of the forefoot when walking or standing, in order to ensure adequate space for unimpeded movement of the toes and to provide protection from side impacts. In some embodiments, this side protection can be enhanced by including an upstanding protective portion 25 that extends upward slightly and curves, forming a cavity to partially enclose one or more toes.

Figure 4:
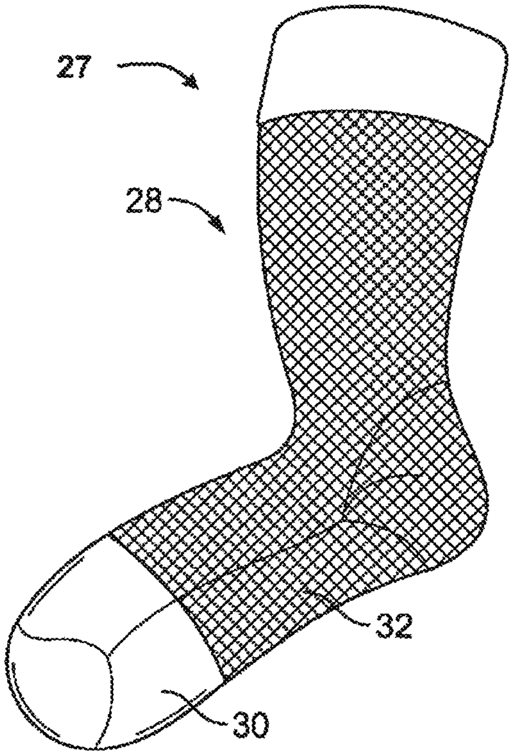
FIGS. 4 and 4A are diagrammatic views of socks according to two implementations.
Figure 6:
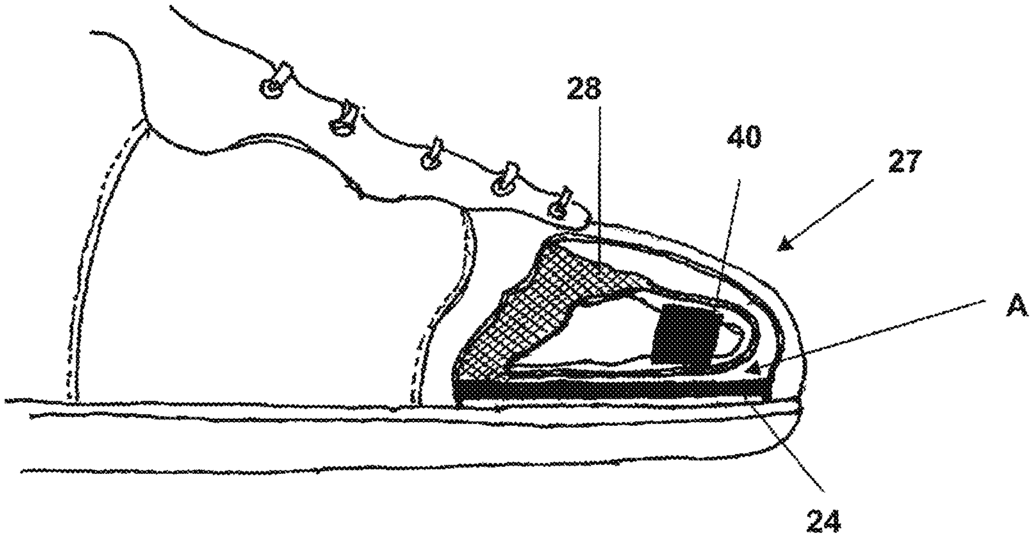
FIG. 6 is a partial cut-away side view of the orthotic support device of FIG. 1 in use with a toe splint.

In use, and as shown in FIG. 6, the liner 24 is disposed juxtaposing an injured musculoskeletal structure and healthy musculoskeletal structures adjacent to the injured musculoskeletal structure. The liner 24 includes a slippery surface 26 that provides an interface having a low coefficient of friction and can be formed of any material that, with the shoe, provides the necessary support for the particular application. The support device 10 additionally includes an inter-face member 27 that covers at least a portion of the wearer's skin to cooperate with the slippery surface 26. As illustrated in FIG. 4, the interface member 27 can be a sock 28 to cover a foot having an injured musculoskeletal structure. Depending on the material of the interface member 27, suitable materials for the slippery surface 26 can include polytetrafluoroethylene, polyethylene, polypropylene, nylon, or the like. In some cases, the liner 24 may be formed of a heat moldable material, to allow the liner to be shaped to portions of the wearer's foot if desired. For example, the liner can be molded to serve as a supportive footbed, providing arch support and/or other ergonomic or therapeutic support to the foot while walking, in addition to providing a slippery surface for mobilization of injured musculoskeletal structures and/or adjacent musculoskeletal structures. One suitable material for use as the liner 24 is commercially available from Sammons Preston (www.sammonspreston.com) under the tradename Aquaplast®.

The stiffness or flexibility of all, or parts of, the support device 10 can be achieved by varying the flexibility of the shoe portion 12 and/or of the liner 24, and can be varied as may be required for treating different conditions. The support device can be or can include portions that are rigid, semi-rigid, or flexible, as appropriate for a given implementation. In most cases, it will be desirable for the support device 10 to be rigid enough to minimize bending motion around the injury site. In some cases, the support device 10 can be supplied to a healthcare provider, or to the end user, with a set of liners 24 having different thicknesses, or other characteristics, to allow the shoe portion 12 to be easily adapted to treat a variety of different injuries or conditions. Similarly, the healthcare provider can be supplied with a plurality of shoe portions 12 having different sizes and/or performance characteristics, to allow the healthcare provider to select a shoe portion 12 to meet a particular patient's needs.

If desired, the liner 24 can include multiple layers, e.g., an upper layer to provide the slippery surface 26 and a lower layer to provide other properties such as cushioning or shock absorption. In such cases one of the layers, e.g., the upper layer, can provide the desired level of stiffness and support. Alternatively, the shoe portion 12 may include a layer of foam or other cushioning material disposed under the liner 24, for example the sole 16 can provide cushioning.

As discussed above, interface member 27 can be formed as a sock 28 of conventional design, and should generally have elastic properties that allow the sock 28 to expand and contract along with the skin of the foot with minimal restriction of the natural expansion or contraction of the foot during standing or walking. In the area A of the injury site (FIG. 6) where unrestrained sliding movement is desired, the fabric of the sock 28 should slide freely and readily on the liner 24, with the interface therebetween having a low coefficient of friction to mobilize the injured toe. Additionally, musculoskeletal structures surrounding the injured toe, such as healthy musculoskeletal structures of the forefoot, including metatarsal structures, are mobilized. Preferably, the sock 28 includes materials or fibers that allow the foot to breathe and allow perspiration to be vented for general health as well as to minimize the possibility of moisture altering the coefficient of friction at the slippery surface 26.

Other physical properties, e.g., elasticity or padding, of one or more areas of the sock 28, or of any interface member 27, can be varied as may be appropriate for differing health conditions.

In some implementations, the liner 24 has one or more slippery areas 26A having a relatively low coefficient of friction, which are disposed juxtaposing the injury site(s), and one or more non-slip areas 29 having a relatively higher coefficient of friction, which are disposed away from the injury site, juxtaposing musculoskeletal structures of the foot that are adjacent to the injury site. For example, the liner can be sized and shaped to juxtapose substantially the entire bot-tom surface of the wearer's foot. An area 29 of the liner 24 that juxtaposes the wearer's heel has a relatively high coefficient of friction to limit the foot sliding forward in the shoe for limiting movement of the liner 24 relative to the heel or other adjacent healthy musculoskeletal structure of the limb. The area 26A of the liner 24 that juxtaposes the toes is slippery and has a relatively low coefficient of friction to allow the toes to move as the foot spreads. In some implementations, the liner 24 can be formed by comolding two different polymeric compositions. Additionally, a separate insole portion can be disposed on the liner to limit sliding of the foot. In other implementations, the liner 24 is sized and shaped such that it does not juxtapose the heel and/or instep of the wearer's foot during use, and sliding between the wearer's heel and/or instep can be limited by the shoe portion 12, as discussed above.

Referring to FIG. 4, a sock 28 has a first region 30 juxtaposing the injury site having a low coefficient of friction, e.g., formed of a synthetic fiber or a combination of fibers or yarns, such as nylon and rayon, such as to provide a low friction interface with the slippery surface 26. A second region 32, e.g., in the heel area, has a relatively higher coefficient of friction. The second region 32 may be formed using a rougher texture knit, and/or using fibers or yams having a higher coefficient of friction. This sock construction allows the toes to slide freely relative to the liner 24 as the foot spreads, while helping to keep the rest of the foot in place within the shoe.

Figure 4A:
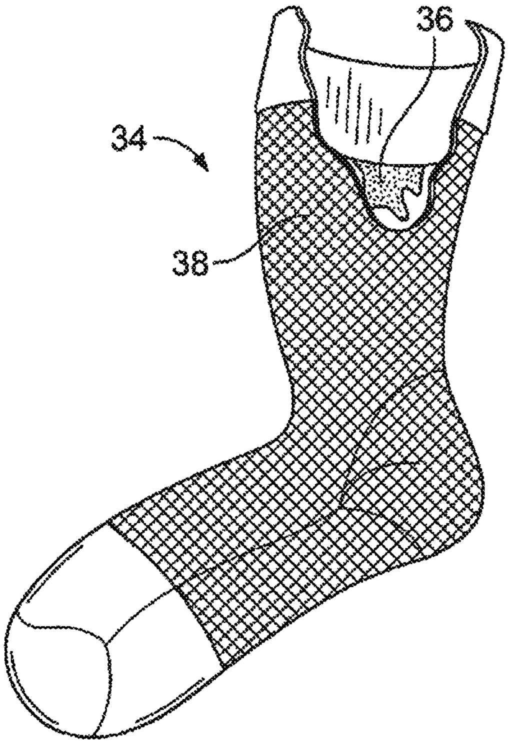

Referring to FIG. 4A, a sock 34 may have two or more layers, to provide desired comfort characteristics. For example, in the embodiment shown the sock includes an inner, moisture wicking layer 36, e.g., of cotton, a cotton blend, or a hydrophilic synthetic material. Also, in some implementations, the sock 28 or the sock 34 can be constructed of the same material, or combination of materials, throughout. In such embodiments, the variations of coefficient of friction are accomplished by variation of portions of the chosen interfacing surfaces.

Now referring to FIG. 6, the interface member 27 can include, integrally or in combination, a splint 40, or other device configured to support an injured musculoskeletal structure, such as a broken phalange of a toe. The splint 40 can be used for localized support, such as to support a joint or to maintain desired alignment of bone portions of the fracture bone, and can be used with or without a fabric covering the splint 40, such as the sock 28. While the splint 40 can be considered an immobilizing device, the slippery surface 26 of the liner 24 still allows the splint 40 to slide freely thereover during standing or walking Additionally, even when the splint 40 is used, phalanges or metacarpals, can be mobilized relative to the slippery surface 26 of the liner 24. The slippery surface 26 can be selected from a material that creates a low friction interface with an external surface of the splint 40, including tape or the like that may be used to attach the splint 40 to the injured musculoskeletal structure. This splint can be rigid, semi-rigid or flexible, and can be formed from any combination of fabrics, foams, suitable metals and/or plastics, such as elastic sleeves, elastic or inelastic bandaging, or conventional splints for digits. To provide sliding interaction, the slippery surface 26 can be formed from polytetrafluoroethylene, polypropylene, or polyethylene, among other materials.

Figure 7:
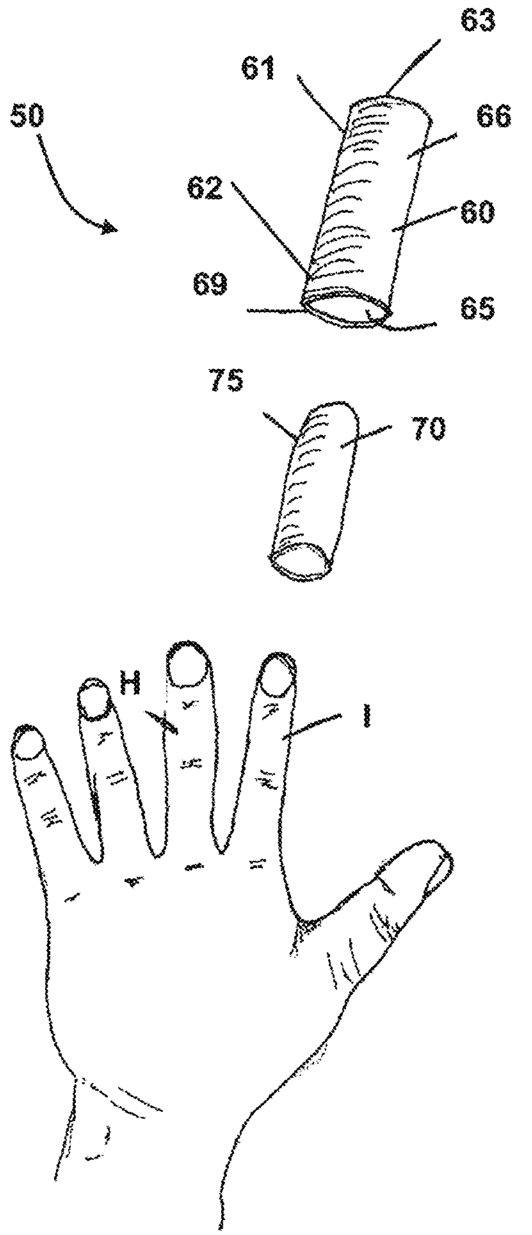
FIG. 7 is an exploded view of another orthotic support device.
Figure 8:
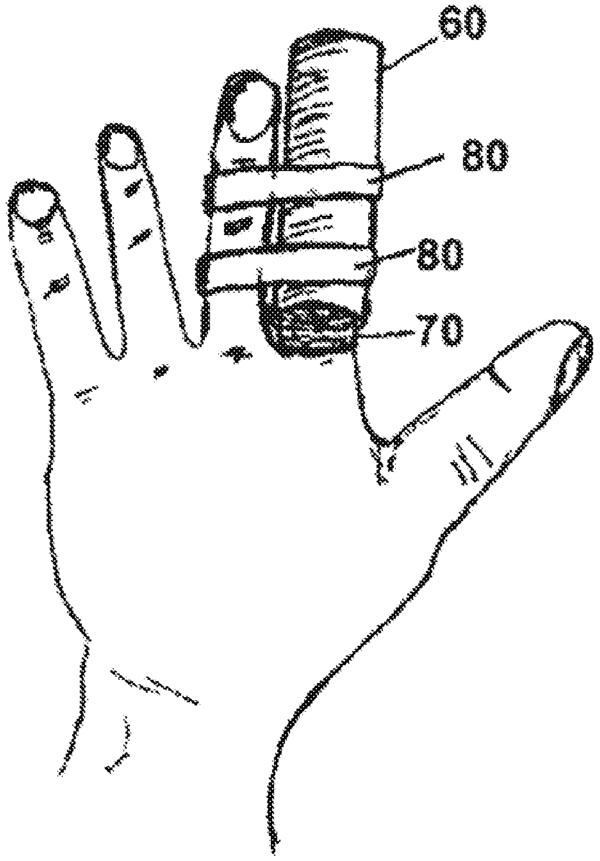
FIG. 8 is a perspective view of the orthotic support device of FIG. 7 in use.

While the support device 10 of FIGS. 1-6 is suitable for mobilizing support of an injured musculoskeletal structure in the foot, including toes and joints, other support devices can be used to mobilize injured musculoskeletal structures of the foot, or of other parts of the body. Referring to FIG. 7, a mobilizing support device 50 includes a rigid digit-receiving support shell 60 and a digit-covering interface member 70 for use in supporting an injured musculoskeletal structure of injured finger I, including injured interphalangeal joints and/or injured metacarpophalangeal joints. As illustrated in FIG. 8, the support shell 60 juxtaposes the phalanges of the injured finger I to reduce injurious contact with foreign objects and undesired bending of the injured finger I. Particularly, the support shell 60 includes a tubular wall 61 having a slippery interior surface 65 and an exterior surface 66. The tubular wall 61 defines a central cavity 69 accessible from at least one open end of the support shell 60. The interface member 70 covers the injured finger I and includes a slippery external surface 75 that slides freely against the interior surface 65 of the support shell 60. The support shell 60 can be formed from any suitable material, including plastics, metals, composite materials, and other materials used for splinting and casting.

In use, and as illustrated in FIG. 8, a wearer, or a nurse, physician, or other caregiver, places the interface member 70 over the injured finger I. As discussed above with respect to the interface member 27, the interface member 70 can include a sock and/or an elastic support material, or other flexible, rigid, or semi-rigid support devices. The wearer or caregiver also places the support shell 60 juxtaposing the injured musculoskeletal structure of the injured finger I. For example, the wearer or caregiver inserts the injured finger I into the support shell 60 such that the support shell partially or fully encloses the injured finger I to protect against injury and to support the injured finger I using an attachment device 80. The wearer or caregiver secures the support shell 60 to an adjacent healthy finger H, or another adjacent healthy musculoskeletal structure of the limb, such as the hand, wrist, or forearm. The support shell 60 can be attached to a contiguous adjacent musculoskeletal structure, such as the palm, that is adjacent to the injured finger, using the attachment device 80. For example, tape, ties, straps, or the like, are used to secure the shell 60 to the healthy finger H for limiting movement of the support shell 60 relative to an adjacent healthy musculoskeletal structure of the limb. Additionally, the interior cavity of the support shell 60 is large enough to provide clearance space between the support shell 60 and the interface member 70 to allow for radial movement of the enclosed interface member 70. The space provided may be from about 0.1" to about 0.3" around the circumference of the interface member. Thus, as the healthy finger H moves, and as the support shell 60 moves with the healthy finger H, the injured finger I is mobilized to move freely within the support shell 60. For additional protection, the distal end of the injured finger I should not extend beyond the distal end of the support shell 60 when in use. The distal end of the support shell 60 can be open, closed, or partially open for ventilation.

Instead of placing the interface member 70 on the injured finger I, the interface member 70 can be attached to the support shell 60 such that the interior surface 65 is covered by the interface member 70. The interface member can be formed from an elastic tubular material such that the interface member 70 narrows within the support shell 60 to cushion the injured finger I during use. For example, the ends of the elastic tubular interface member 70 can be attached to the ends 61 and 62 of the support shell 60 such that the middle portion of the tubular elastic interface member 70 is free to slide over and move within the interior surface 65 of the support shell 60. Thus, the support shell 60 and the interface member 70 in such a configuration can mobilize the injured finger by suspending, cushioning, and sliding. Furthermore, the support shell 60 can be sized such that the injured finger I can move with minimized contact with the interior surface 65 of the support shell 60. For additional protection, the distal end of the injured finger I should not extend beyond the distal end of the support shell 60 when in use. The distal end of the support shell 60 can be open, closed, or partially open for ventilation.

As illustrated in FIGS. 9-9B, a support device 50A includes a tab 90A included with the support shell 60A. The tab 90A provides secure attachment to the wearer's hand H using the attachment device 80. The tab 90A can be rigid or resilient to limit or inhibit bending of the injured finger I. Alternatively, the tab 90A can be flexible such that the tab 90A does not inhibit bending of the injured finger I at the metacarpophalangeal joint. Support devices with different characteristics may be indicated for different applications. For example, the tab 90A can be shaped to extend beneath one or more metacarpal heads depending on the circumstances.

Figure 10:
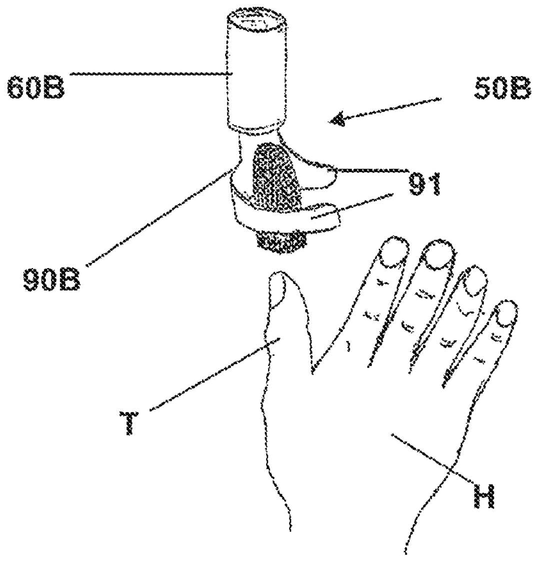
FIG. 10 is an exploded view of another orthotic support device.
Figure 10A:
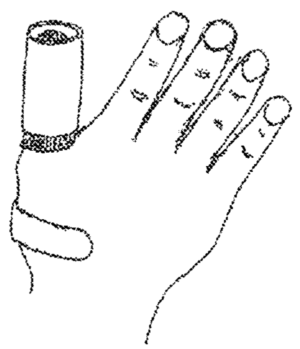
FIGS. 10A and 10B are perspective views of the orthotic support device of FIG. 10 in use.
Figure 10B:
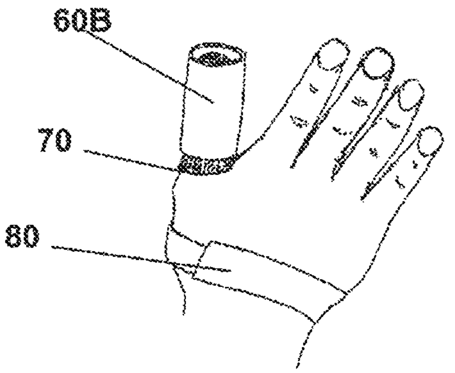

As illustrated in FIGS. 10-10B, a support device 50B supports an injured thumb T. The tab 90B is configured as a body-engaging clip with arms 91. The arms 91 are resilient and deformable to fit over the wearer's hand H. The arms 91 exert a retaining force, such as by spring action, to secure the support device 50B to the wearer's hand H, as shown in FIG. 10A. Additionally or alternatively, as shown in FIG. 10B, the support device 50B can be retained in a position juxtaposing the injured musculoskeletal structure of the thumb T using the attachment device 80 wrapped around and/or adhered to the hand H. The tab 90B can be modified or extended to provide varying engagement or attachment with the hand, wrist or arm as deemed appropriate for a particular condition.

Figure 11:
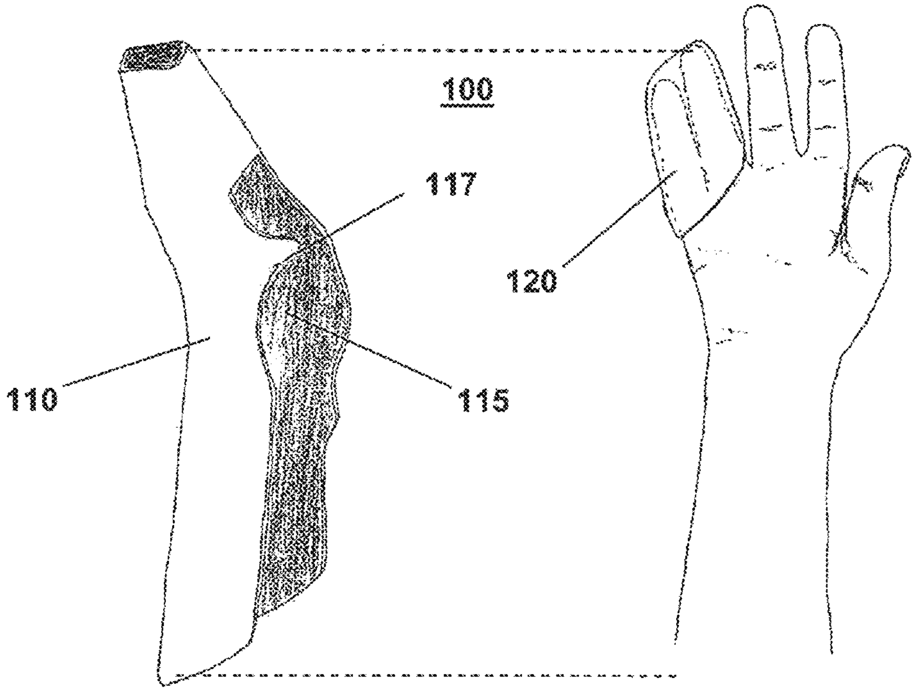
FIG. 11 is an exploded view of another orthotic support device.
Figure 11A:
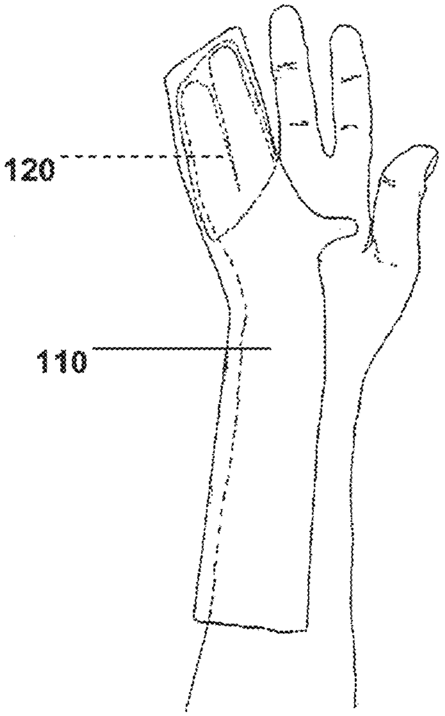
FIG. 11A is a perspective views of the orthotic support device of FIG. 11 in use.

Referring now to FIGS. 11 and 11A, a support device 100 includes a contoured support shell 110 that, in use and as illustrated in FIG. 11A, juxtaposes musculoskeletal structures in the wearer's arm, wrist, and hand, including fingers. The support shell 110 can be used to support, for example, a fractured metacarpal bone adjacent to the arm, wrist and hand. Thus, the support shell 110 is sufficiently rigid to protect the fracture site. The support device 100 also includes an interface member 120 for covering the finger adjoining the fractured bone, and one or more fingers adjacent thereto. The support shell 110 includes a slippery interior surface 115 to allow the interface member 120 to slide freely thereover to mobilize the fingers adjoining the fractured bone relative to the support shell 110. Thus, when the interface member 120 is placed over the finger adjoining the fracture and over the adjacent finger and when the support shell 110 is placed juxtaposing the fracture site, as illustrated in FIG. 11A, the interface member 120 mobilizes the fingers to slide freely over the slippery interior surface 115 to reduce forces applied to the fractured metacarpal bone as the fingers are flexed, or as the hand or arm pushes forward or pulls rearward in the support shell. For additional protection, the distal end of the interface member 120 does not extend beyond the distal end of the support shell 110 during use. The distal end of the support shell 110 can be open, closed, or partially open, such as including perforations or other ventilating structure.

The support shell 110 also includes a tab 117 that retains the support device 110 in position on the wearer's hand and arm. For example, the tab 117 can press inward against the wearer's hand to apply a retaining force. Alternatively, the tab 117, and/or other portions of the support shell 110 can include a tacky surface that adheres to the wearer's skin. Alternatively, the support device 100 can be secured using a strap, tape, or other attachment device.

Figure 12:
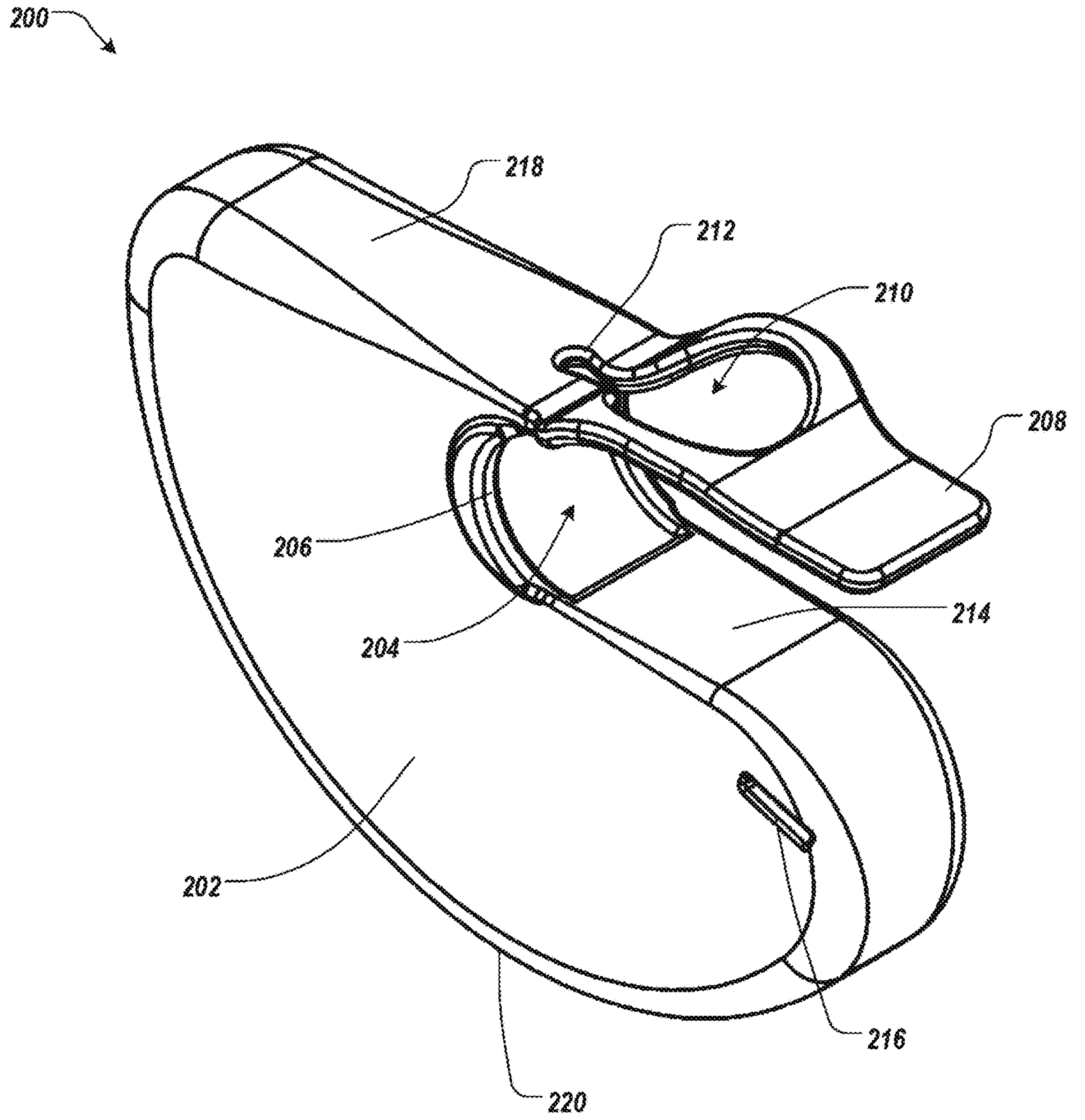
FIG. 12 is a perspective view of a finger enclosure.

Referring to FIG. 12, a finger enclosure 200 includes a protective shell 202 for enclosing a finger. The protective shell 202 can provide a finger having musculoskeletal and/or skin injury with protection from outside forces and elements while allowing the finger to substantially maintain a desired natural range of motion within the shell 202. The enclosure 200 may be worn, for example, while the patient is sleeping. In some cases, the protective shell 202 allows the finger to move freely within the shell 202 in a direction parallel to a sagittal plane of the hand while limiting medial-lateral movement out of the plane. The protective shell 202 can be formed from any rigid, semi-rigid, or flexible material, including plastics, metals, composite materials, as well as other materials used for splinting and casting. The protective shell 202 can be configured such that it is neither attached to nor compressed against the protected finger or a portion of the protected finger. The protected or enclosed finger may refer to any of the fingers, including the thumb.

The protective shell 202 includes an opening 204 for receiving a finger into an interior cavity defined by the shell 202. The opening 204 is oriented generally in the proximal-distal direction and can have edge portions 206 that are curved to conform to a user's hand. In some cases, the edge portions 206 can be thickened to reduce stress on contacting portions of the hand to, for example, increase comfort of the user while wearing the enclosure 200.

Figure 13A:
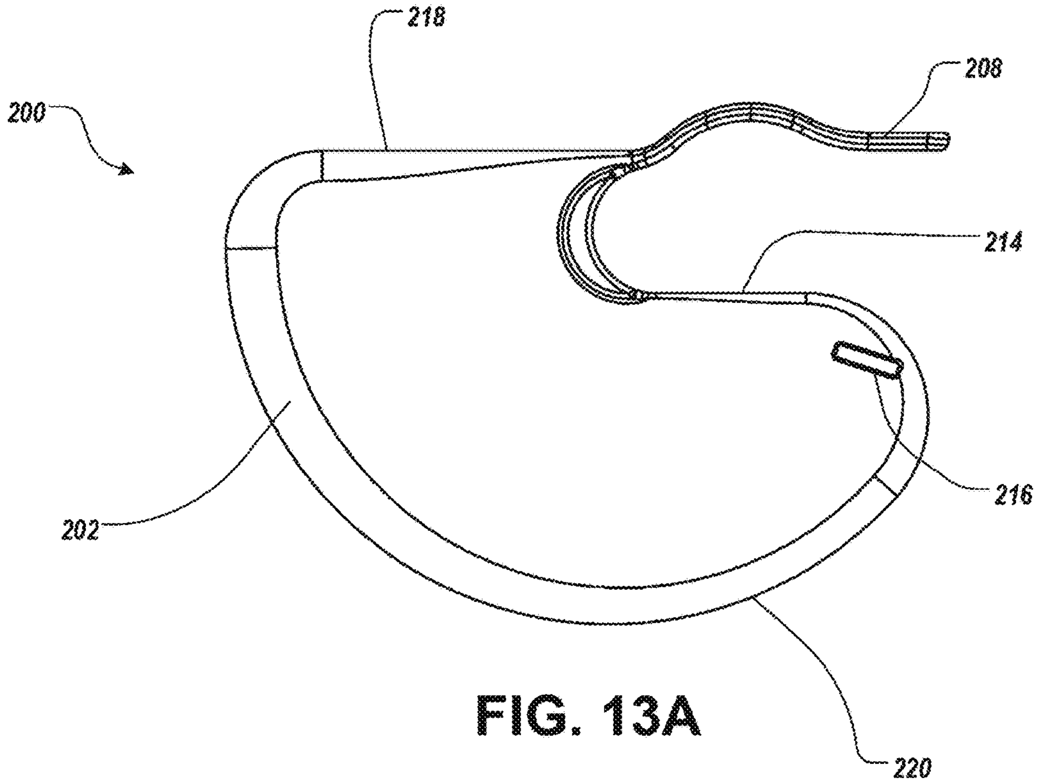
FIGS. 13A and 13B are side and top views of the finger enclosure of FIG. 12.

Referring also to FIG. 13A, the protective shell 202 can include a dorsal tab 208 to help attach the enclosure 200 to the user's hand. As shown, the dorsal tab 208 is a generally flat structure that extends in a proximal direction from near an upper side of the opening 204. The dorsal tab 208 is designed to contact a dorsal side, i.e. posterior or back side, of the hand to provide a securing point for an attachment device, which will be described further below. In some implementations, the dorsal tab 208 can be contoured to conform to a knuckle portion of the finger being inserted into the enclosure 200. In some implementations, the dorsal tab 208 may include a surface that provides resistance to sliding motion at portions where said surface contacts the dorsal side of the hand.

Figure 13B:
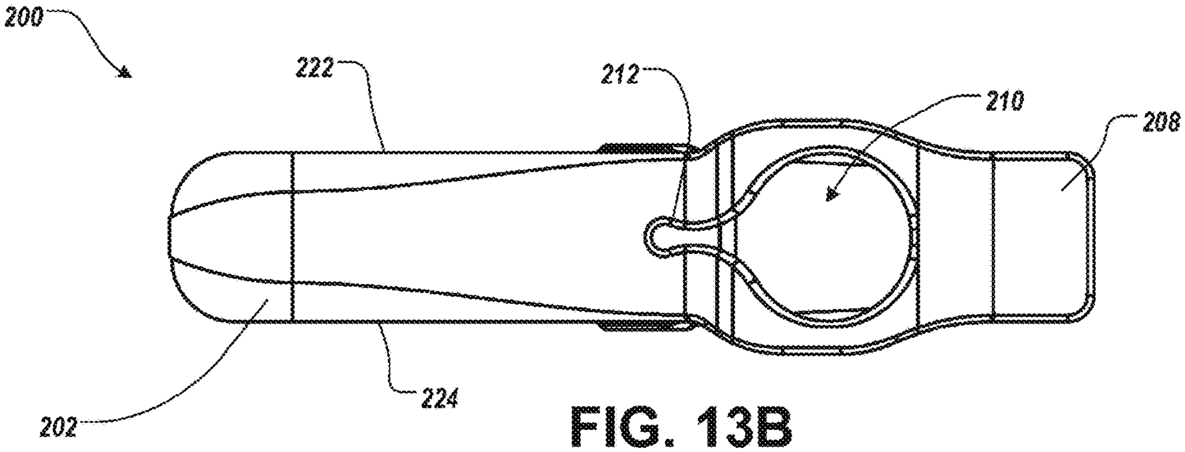

In some implementations, as also shown in FIG. 13B, the dorsal tab 208 can include an opening 210 for receiving an interface member (as discussed below). As further detailed below, an open end portion of the interface member can be pulled through the opening 210 and secured in a nook 212 to hold the interface member in place and limit sliding of the interface member along the finger.

Referring again to FIG. 12, an outer surface of the protective shell 202 can include a supporting portion 214 positioned proximally adjacent to the opening 204. The supporting portion 214 can help secure and stabilize the protective shell 202 relative to the user's hand by pushing up against and supporting a base of the finger being inserted into the opening 204. Additionally, or alternatively, the supporting portion 214 can push up against the palm of the user's hand to provide support. In some implementations, the protective shell 202 defines slots 216 on either side of the shell 202. To help attach the device to the hand, an attachment device, including but not limited to a tab, a tape, a strap, a tie, a clip, and a hook-and-loop fastener, can be inserted into the slots 216 at a volar side, i.e. anterior or palm side, of the hand and looped around the dorsal tab 208 on the dorsal side of the hand. The protective shell 202 can also define one or more ventilation slots.

As noted above, the protective shell 202 can allow the finger to move freely within the shell 202, for example throughout all or a part of the finger's natural range of motion, without coming into contact, or at least not in substantial contact with the shell 202 that would cause discomfort to the user. Additionally, because the protective shell 202 is generally attached to the hand without being attached to the protected finger, impacts or external forces exerted against the protective shell 202 can be absorbed at portions where the device is attached to the hand, thereby resulting in minimized transfer of impact or other forces to the protected finger. By shaping the protective shell 202 to have a substantially flat top portion 218 and a substantially arcuate bottom portion 220, an overall size of the protective shell 202 that allows this type of finger movement can be minimized. In some implementations, an outline defined in part by the flat top portion 218 and the arcuate bottom portion 220 can correspond to a complete movement locus of the finger as it moves from a fully extended position to a fully flexed position.

Referring again to FIG. 13B, the protective shell 202 can include two substantially parallel sidewalls 222, 224 that, once the enclosure 200 has been attached to the patient's hand, are each substantially parallel to the sagittal plane of the hand. In some cases, the sidewalls 222, 224 are sufficiently spaced apart from each other to provide clearance space on one or both sides of the finger. In some cases, the sidewalls 222, 224 may be placed closer together such that the lateral motion of the finger is substantially limited.

Figure 14:
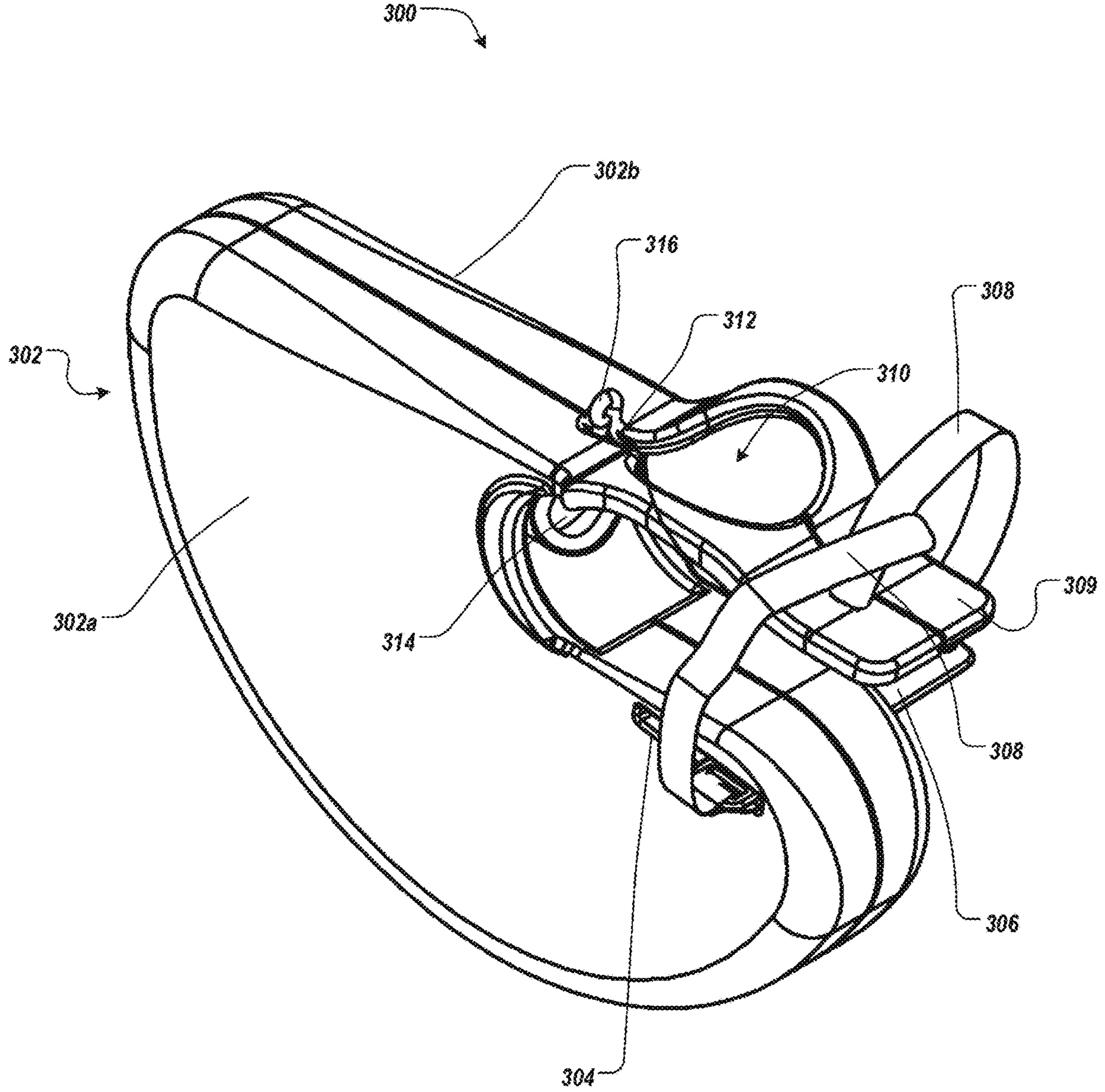
FIG. 14 is a perspective of an enclosure device.
Figure 15:
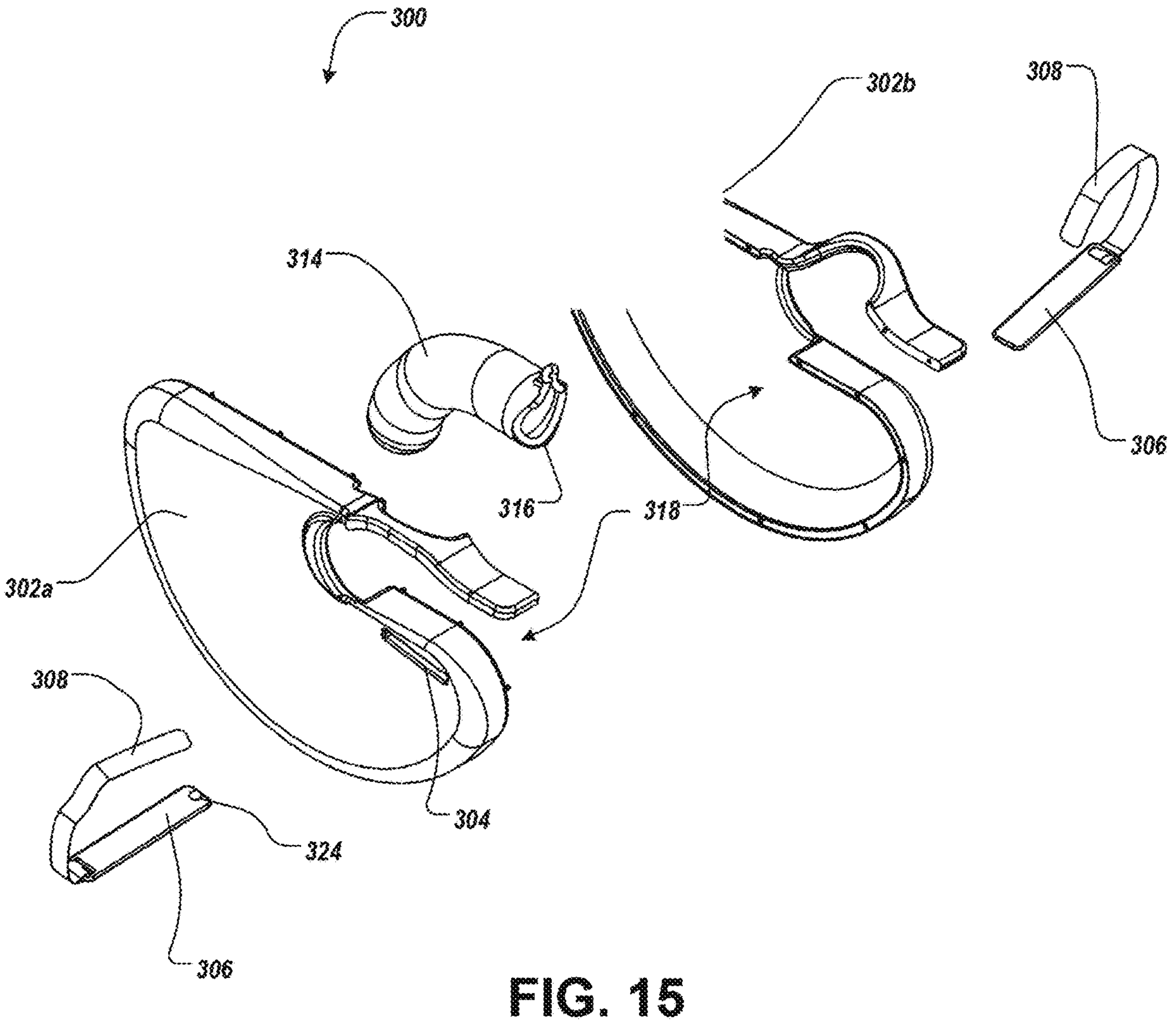
FIG. 15 is an exploded view of the enclosure device of FIG. 14.

While the protective shell 202 in FIGS. 12 and 13 is illustrated as being a unitary piece, the shell 202 may be assembled from two or more pieces. For example, FIGS. 14 and 15 illustrate an alternative enclosure device 300 having a protective shell 302 formed from two separate pieces 302*a*, 302*b* that are joined. The pieces 302*a*, 302*b* may be joined to each other by, for example, gluing, press-fitting, welding, and snap-fitting, among others. Each piece 302*a*, 302*b* defines a corresponding portion of an interior cavity 318 of the shell 302.

Referring to FIGS. 14 and 15, the device 300 includes a slot 304 into which a pair of stabilizing tabs 306 can be inserted. As a result, each stabilizing tab 306 can be positioned to protrude laterally outward from a side surface of the protective shell 302. The stabilizing tabs 306 help to attach and secure the device 300 to the user's hand. For example, instead of directly looping the attachment device 308—which can include a tab, a tape, a strap, a tie, a clip, and a hook-and-loop fastener, among others-through the slot 304, the attachment device 308 can be attached to either ends of the tabs 306 as shown in FIGS. 14 and 15. For example, the ends of the tabs 306 can include slots for receiving the attachment device 308. In some cases, the tabs 306 may be integrated to the attachment device 308. Additionally, the protruding tabs 306 can aid in stabilizing the device 300 by spreading out the contact area with the hand and helping to reduce twisting of the protective shell 302 relative to the hand. The attachment device, with or without stabilizing tabs, can be used with the configurations of FIGS. 12 and 14.

As illustrated in FIGS. 14 and 15, the device 300 can include an interface member 314. The interface member 314 covers the finger and can include a slippery external surface that facilitates sliding against an interior surface of the protective shell 302. The interface member 314 may be pre-positioned inside the device 300 prior to insertion of the finger, or alternatively, the interface member 314 may first be placed around the finger prior to insertion. In some cases, the interior surface of the protective shell 302 can additionally or alternatively include a slippery inner surface adapted to provide a low friction interface between the shell and the finger. Similar to the enclosure 200, the device 300 can include a dorsal tab 309 having an opening 310 and a nook 312.

The interface member 314 can be in the shape of a tube or a sock and can be made from an elastic support material, or other flexible materials. The interface member 314 may have a rolled edge 316 that is designed to be positioned near a base portion of the finger. To keep the interface member 314 from sliding up the finger during, for example, repeated bending and unbending of the finger within the shell 302, a portion of the rolled edge 316 can be secured to the dorsal tab 309 as illustrated in FIG. 14. In use, a portion of the rolled edge 316 can be pinched and pulled through the larger opening 310, after which the pinched portion can be held in place by further threading through the narrower nook 312 on a distal side of the opening 310. The interface member 314 may be attached to a portion of the protective shell 302 in various other ways to hold the interface member 314 in position on the protected finger while the device 300 is in use.

Figure 16A:
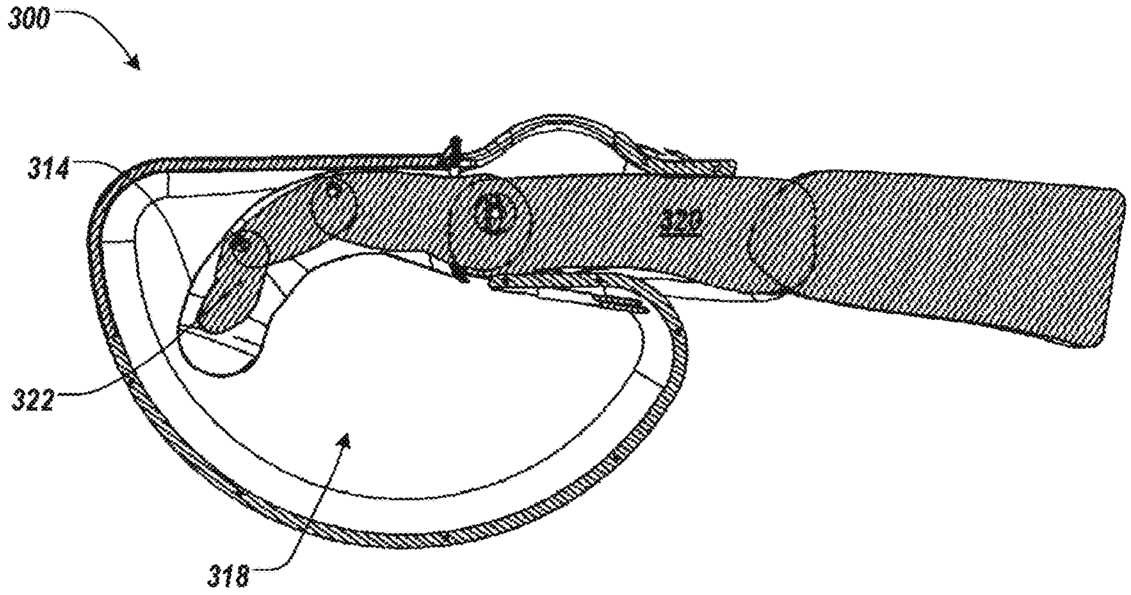
FIGS. 16A and 16B are side cross-sectional views of the enclosure device of FIG. 14 in use.
Figure 16B:
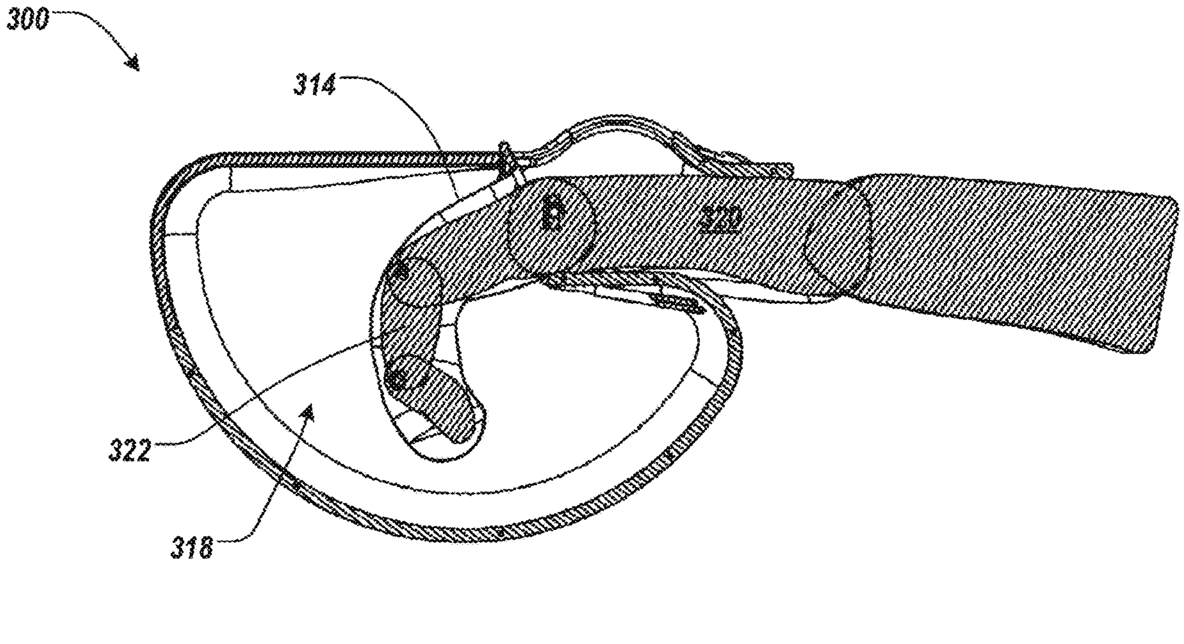

The movement of a finger 322 within the interior cavity 318 of the device 300 is illustrated in FIGS. 16A and 16B, where the device 300 is shown attached to a dorsal and a volar side of a user's hand 320. As depicted in the illustration, the interior cavity 318 is shaped and sized to allow the finger 322 to fully extend and flex within the sagittal plane of the hand. In some implementations, the interior cavity 318 forms a substantially semi-cylindrical volume within the protective shell 302.

Figure 17A:
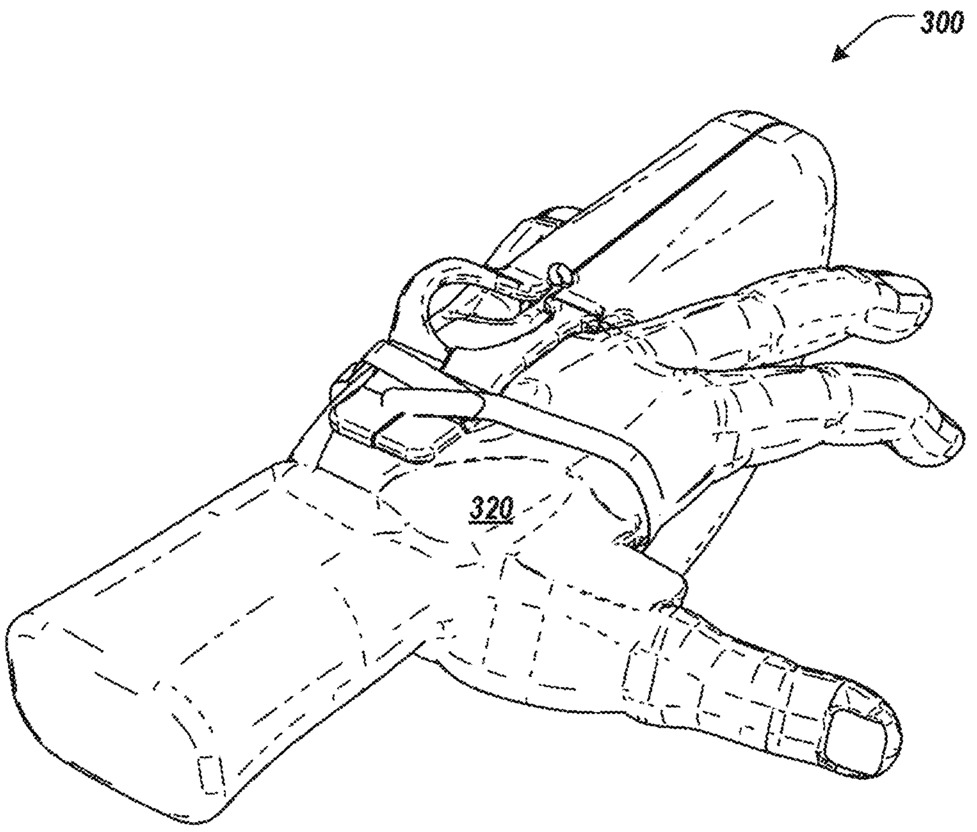
FIGS. 17A and 17B are perspective and side views of the enclosure device of FIG. 14 in use.
Figure 17B:
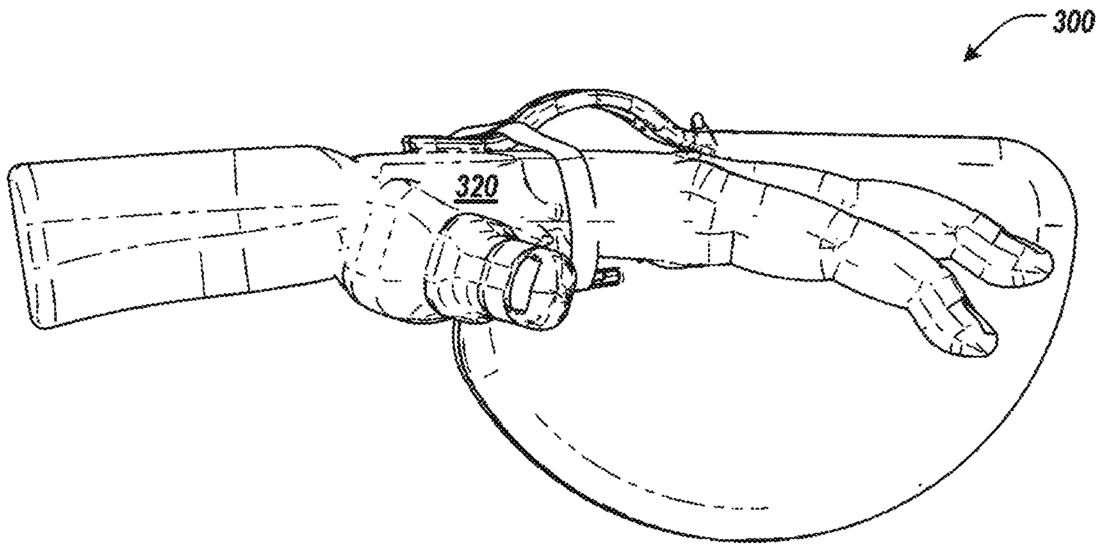
Figure 18A:
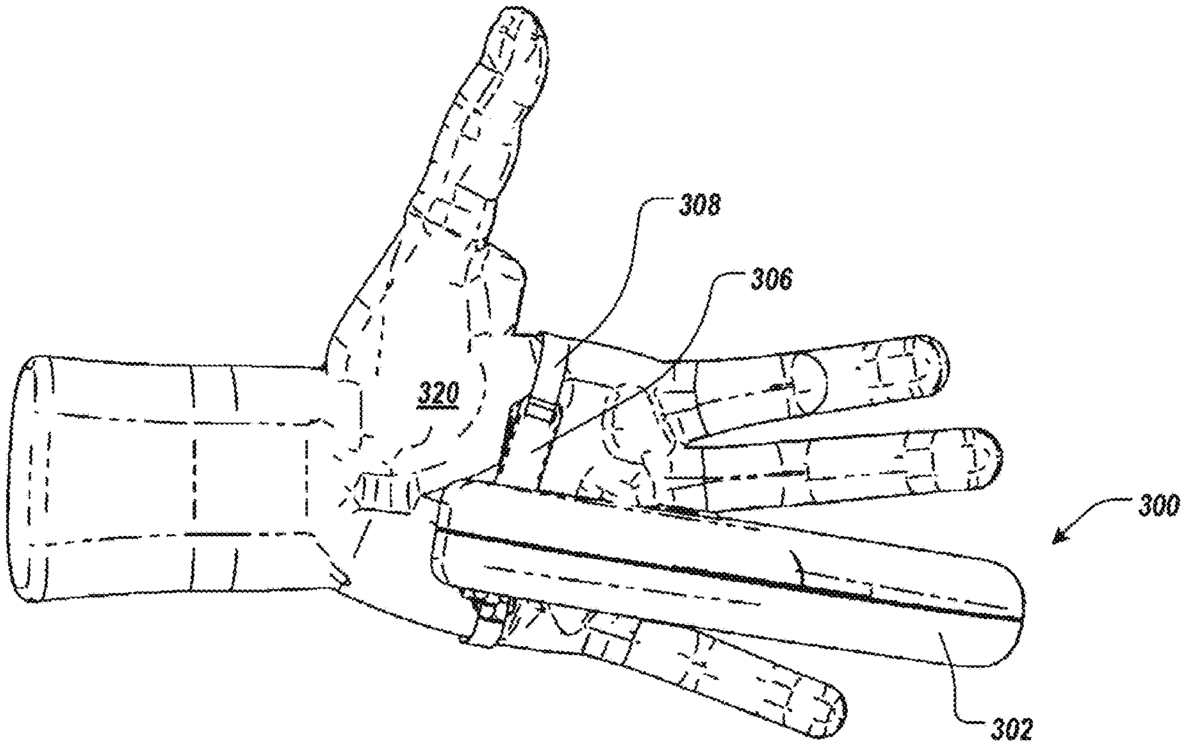
FIGS. 18A and 18B are top views of the enclosure device of FIG. 14 in use.
Figure 18B:
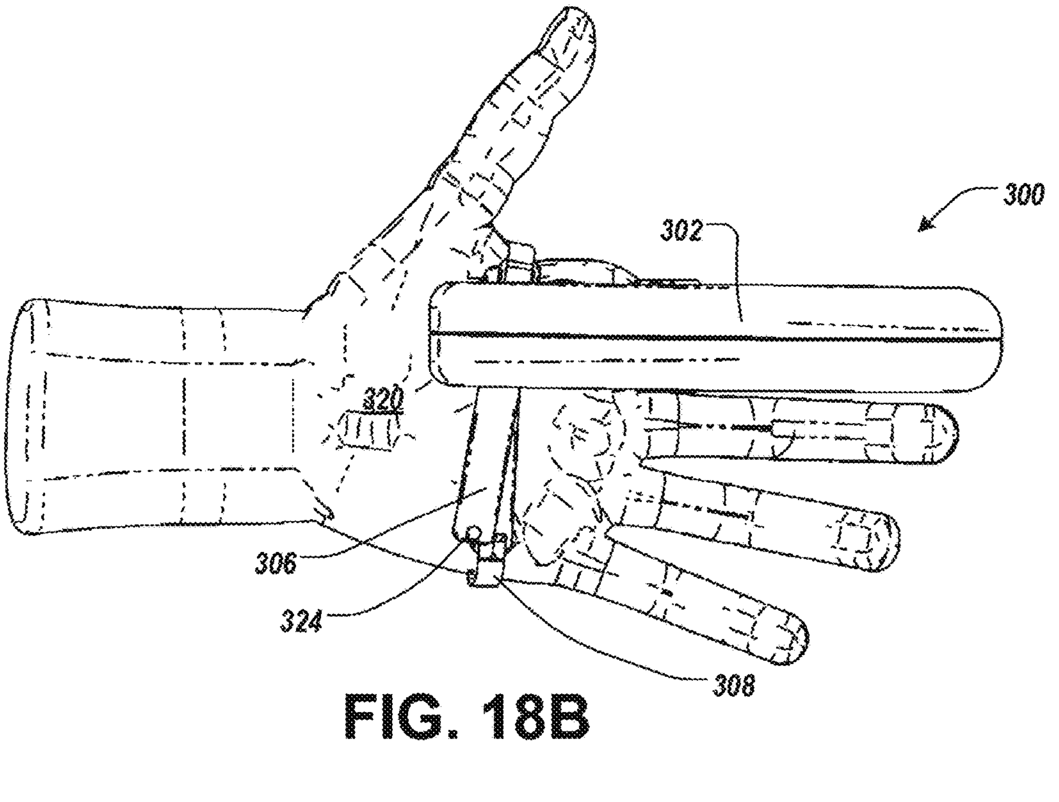

Referring to FIGS. 17A and 17B, the device 300 is shown attached to the hand 320. While the device 300 is shown enclosing the fourth finger, other fingers may be similarly enclosed by the device 300. FIGS. 18A and 18B illustrate the device 300 as attached to the left hand 320 and enclosing, respectively, the fourth (i.e. ring) and second (i.e. index) fingers. The pair of stabilizing tabs 306, each of which protrude medially-laterally outward from the protective shell 302, can be moved medially and laterally relative to the shell 302 such that the stabilizing tabs maintain contact with the hand 320 regardless of the position of the shell 302 A bump 324 on each tab 306 can help prevent the tab 306 from sliding completely out of the slot 304 (FIG. 15).

FIGS. 19 to 27 show various implementations of an adjustable enclosure device that can be worn around a musculoskeletal structure such as a finger by attachment to another part of the body, avoiding attachment or compression between the enclosure device and all or part of the enclosed musculoskeletal structure.

Figure 19:
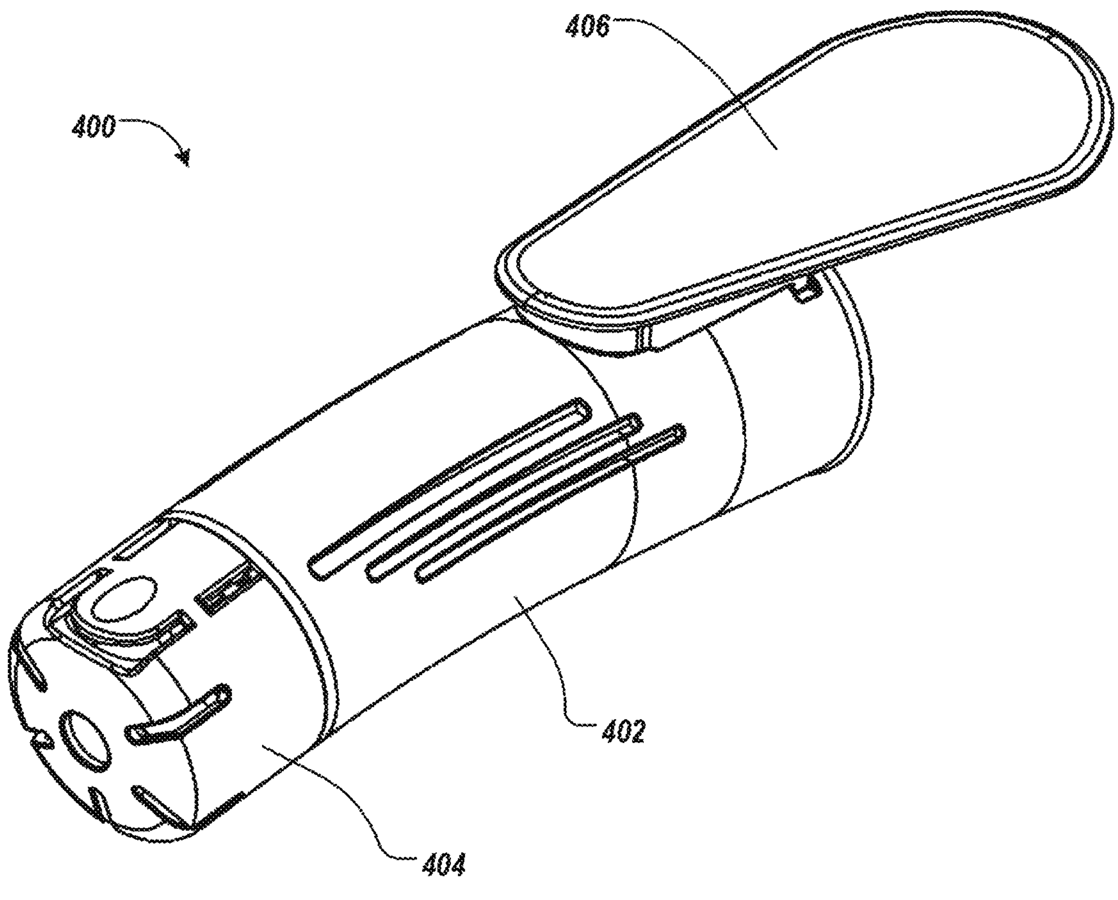
FIG. 19 is a perspective view of another enclosure device.

Referring to FIG. 19, an adjustable enclosure device 400 includes a tubular portion 402 and an end cap portion 404. The end cap portion 404 is removably coupled to the tubular portion 402 as further discussed below. In some implementations, a knuckle guard 406 is attached to a dorsal side of the tubular portion 402 and extends proximally beyond a proximal end of the tubular portion 402. As described further below, the knuckle guard 406 can help secure the device 400 to the user's hand as well as provide further protection to a knuckle region of the enclosed finger. The device 400 can be attached to parts of the body, for example the user's hand, without being attached to the enclosed finger.

Figure 20A:
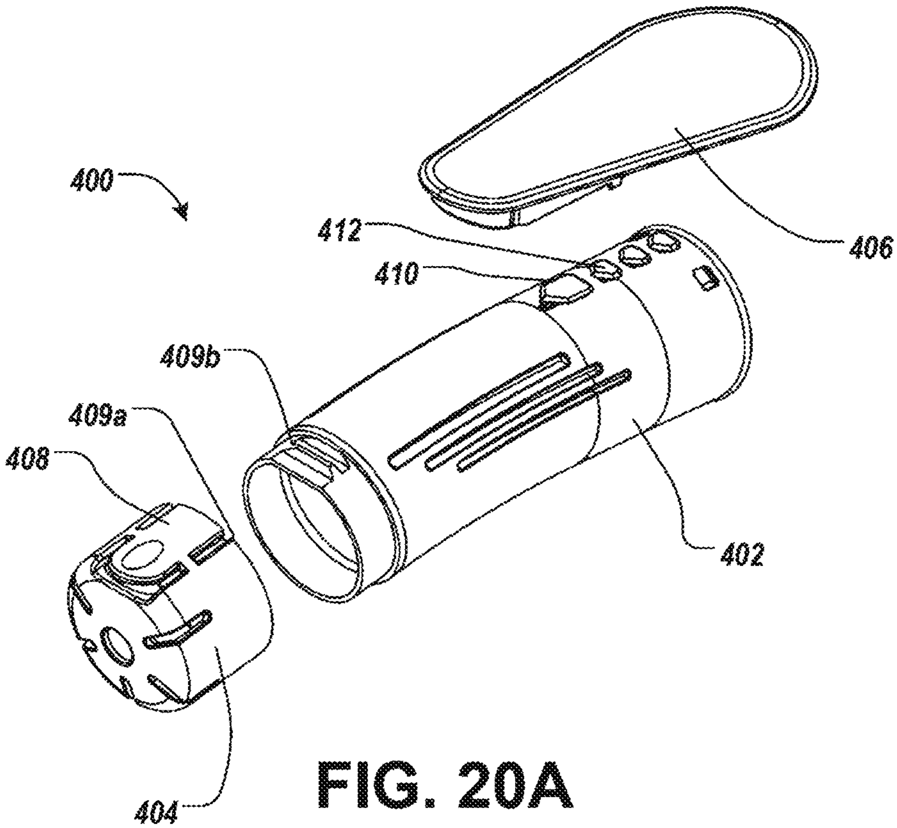
FIGS. 20A and 20B are exploded perspective and side views of the enclosure device of FIG. 19.
Figure 20B:
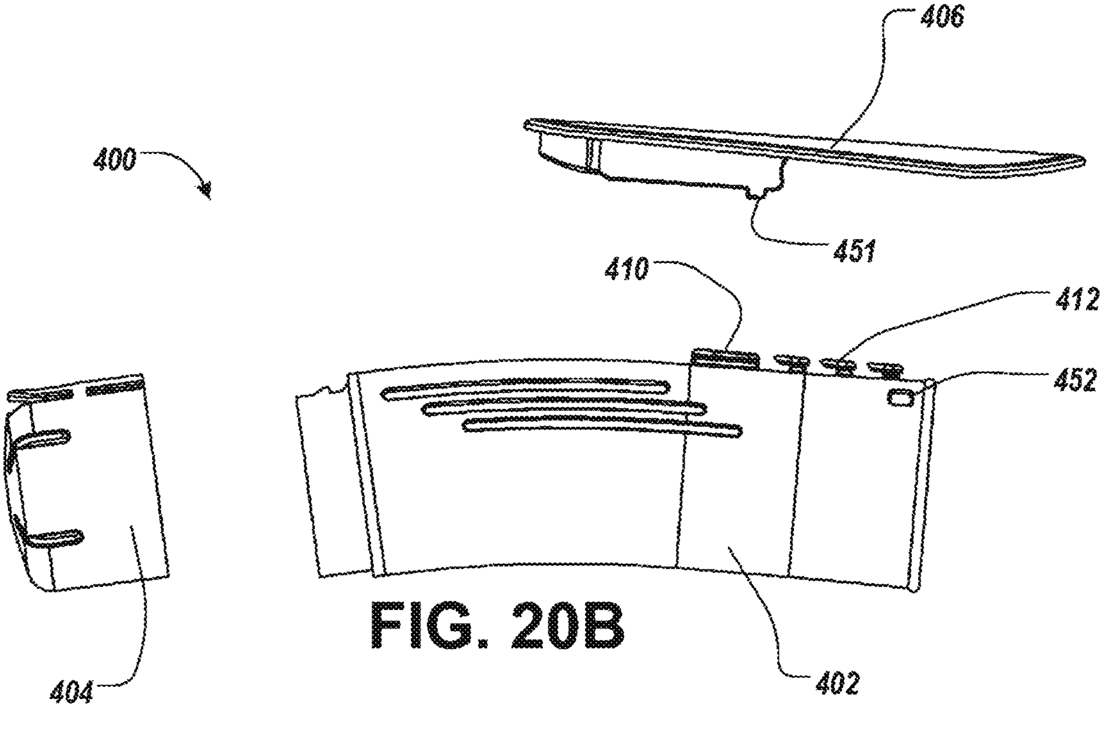

Referring also to the exploded view of the device 400 shown in FIGS. 20A and 20B, the end cap portion 404 can be coupled to a distal end of the tubular portion 402 via a latch mechanism 408. The latch mechanism 408 is a pivoting structure that is integrally or separately attached to the end cap portion 404. An engaging latch 409*a* on a bottom side of the latch mechanism 408 is configured to latch onto a corresponding receiving latch 409*b* on the tubular portion 404, for example, when the end cap portion 404 is slid over the tubular portion 402. The end cap portion 404 can be removed from the tubular portion 402 by, for example, pressing down on a distal end of the latch mechanism 408 to release the engagement between the latches 409*a* and 409*b*. Various types of coupling between the end cap portion 404 and the tubular portion 402 may also be used, including but not limited to snap-fit, interference-fit, and screw-fit.

Figure 21:
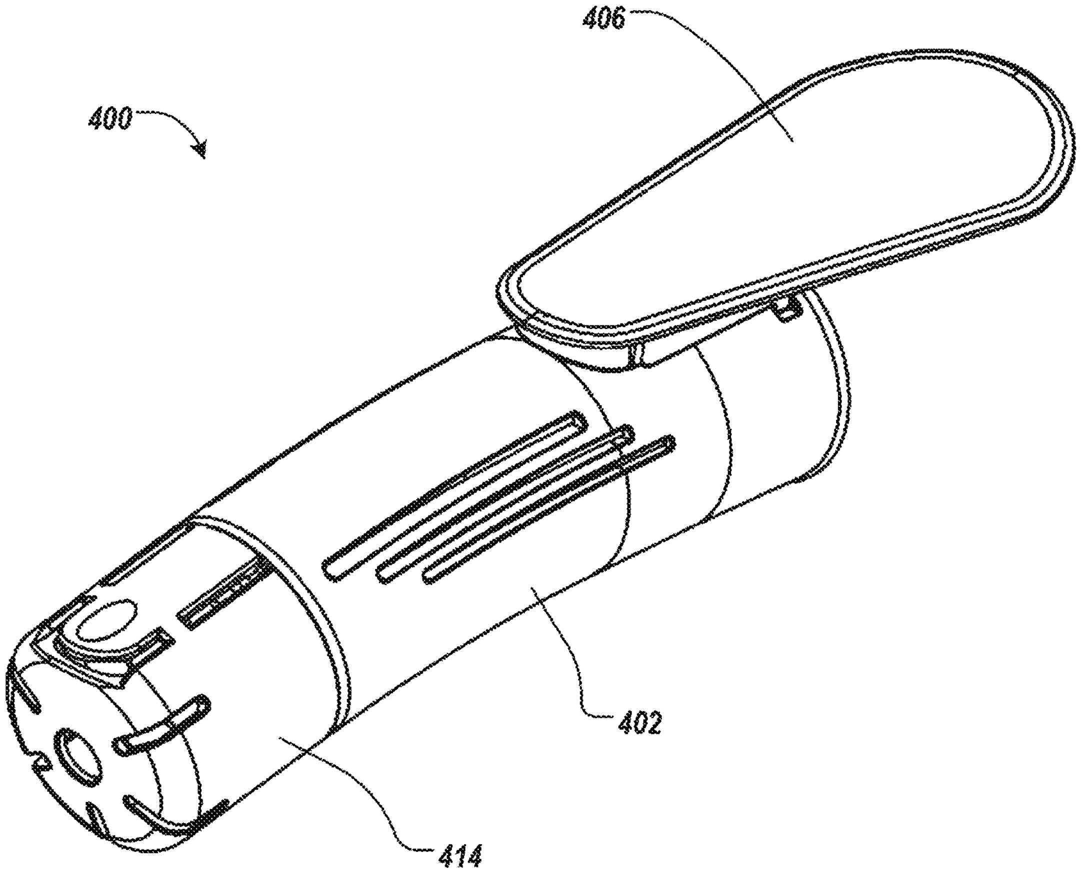
FIG. 21 is an alternative implementation of the enclosure device of FIG. 19.

In use, the device 400 can be worn around the finger such that the tubular portion 402 juxtaposes multiple phalanges of the finger. A portion of the finger extending distally beyond a distal end of the tubular portion 402 is enclosed by the end cap portion 404. To accommodate fingers of varying lengths and/or adjustable positioning of the tubular portion 402 along a length of the finger, different sized end cap portions can be used. For example, FIG. 21 shows the tubular portion 402 coupled to an extended length end cap portion 414. End cap portions of varying lengths can be provided in a kit with the tubular portion 402.

Referring again to FIGS. 20A and 20B, the knuckle guard 406 can be coupled to the tubular portion 402 by sliding the knuckle guard 406, for example in the distal-proximal direction, over a securing member 410 and snapping the knuckle guard 406 in place. For example, as further depicted in FIG. 22C, the securing member 410 includes a rail portion 450 that slides into a correspondingly configured slot on a bottom side of the knuckle guard 406. Once the knuckle guard 406 has been slid to a predetermined location, tabs 451 protruding downwardly from the knuckle guard 406 can snap into correspondingly configured slots 452 in the tubular portion 402 (FIG. 20B). In addition to the securing member 410, the tubular portion 402 can also include a series of securing hooks 412 for securing an open end portion of an interface member (see description below relating to FIG. 25B). Because the knuckle guard 406 can be configured to slide over the securing member 410 in a distal-proximal direction, the interface member may be secured to the tubular portion 402 prior to installation of the knuckle guard 406.

Figure 22:
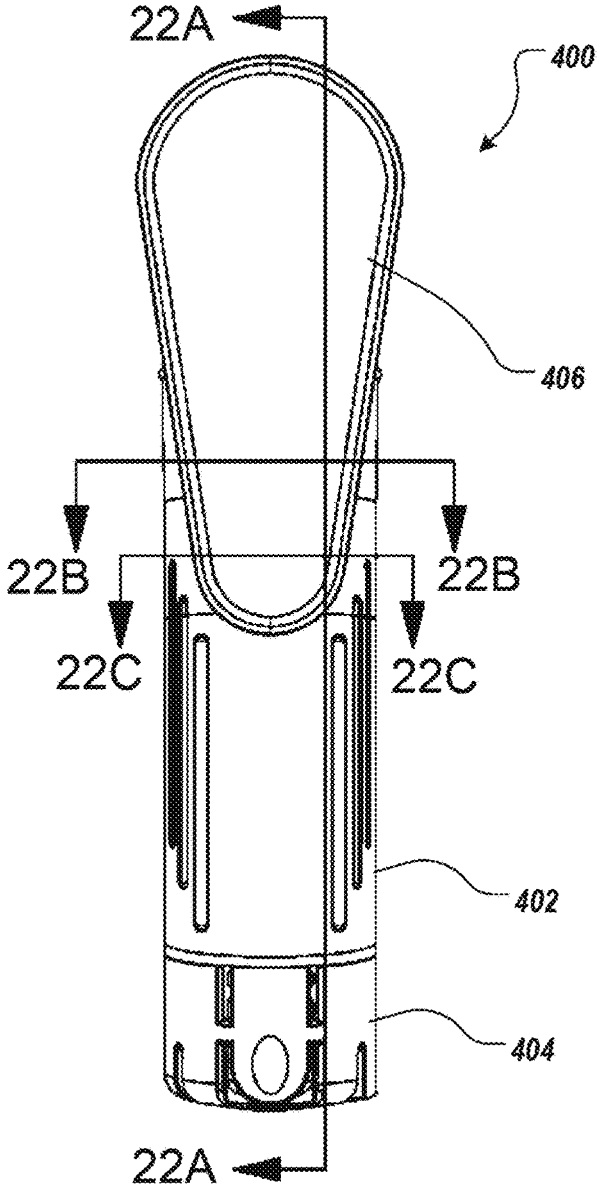
FIG. 22 is a top view of the enclosure device of FIG. 19.
Figure 22A:
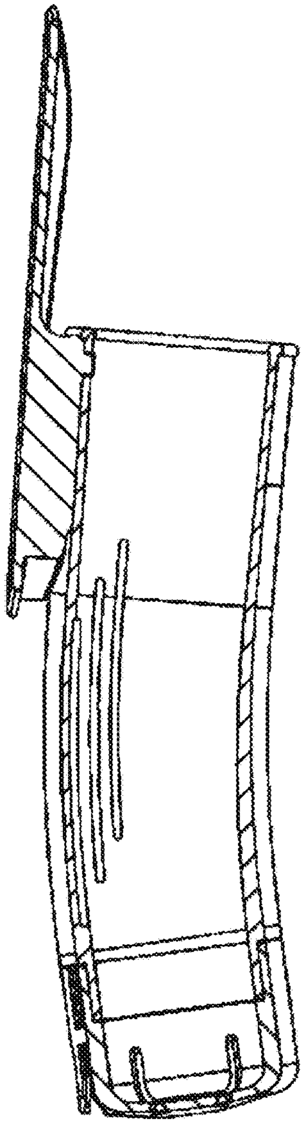
FIGS. 22A-22C are cross-sectional views of FIG. 22.
Figure 22B:
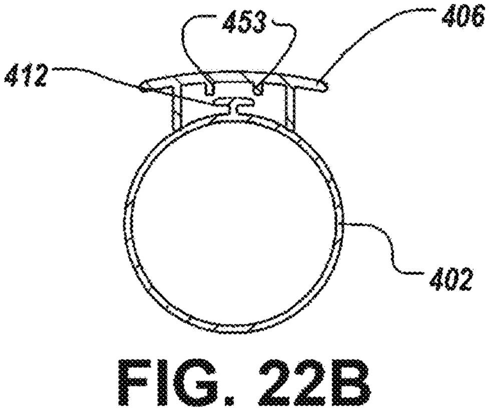
Figure 22C:
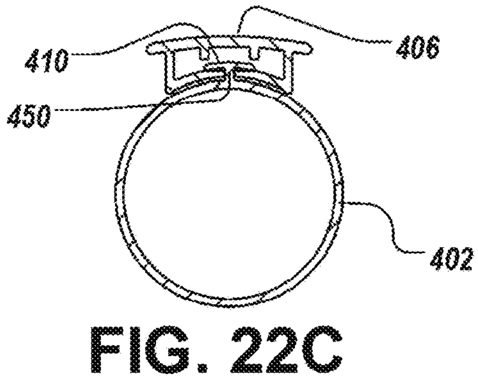

Referring also to FIG. 22 and the cross-sectional views thereof shown in FIGS. 22A-C, the knuckle guard 406 is shown secured to the tubular portion 402. As shown in FIG. 22C, the knuckle guard 406 includes a narrow slot that is sized to receive the rail portion 450 of the securing member 410, thereby securing the knuckle guard 406 to the tubular portion 402. The knuckle guard 406 can also include guardrails 453 that protrude downwardly toward the securing hooks 412. Once the interface member has been secured to the securing hooks 412, as will be detailed below, the guardrails 453 can help prevent the interface member from becoming disengaged.

Figure 23A:
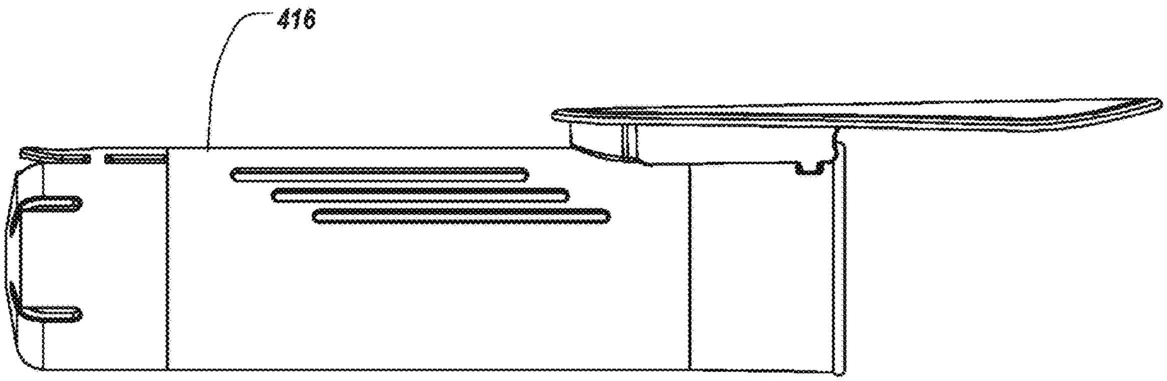
FIGS. 23A and 23B are side views of alternative implementations of the enclosure device of FIG. 19.
Figure 23B:
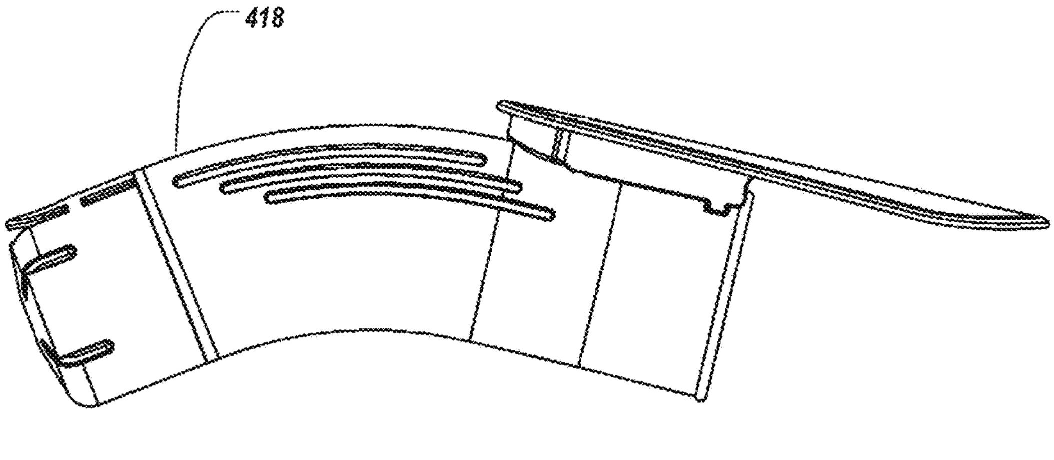

While the tubular portion 402 of the device 400, as depicted in FIG. 19, was shown to be slightly curved along its longitudinal axis, this curvature may be greater or less depending on, for example, the user's anatomy and/or the nature of the injury. For example, as illustrated in FIG. 23A, a tubular portion 416 may be substantially straight. Conversely, as illustrated in FIG. 23B, a tubular portion 418 may have a greater curvature along the longitudinal axis.

Figure 24A:
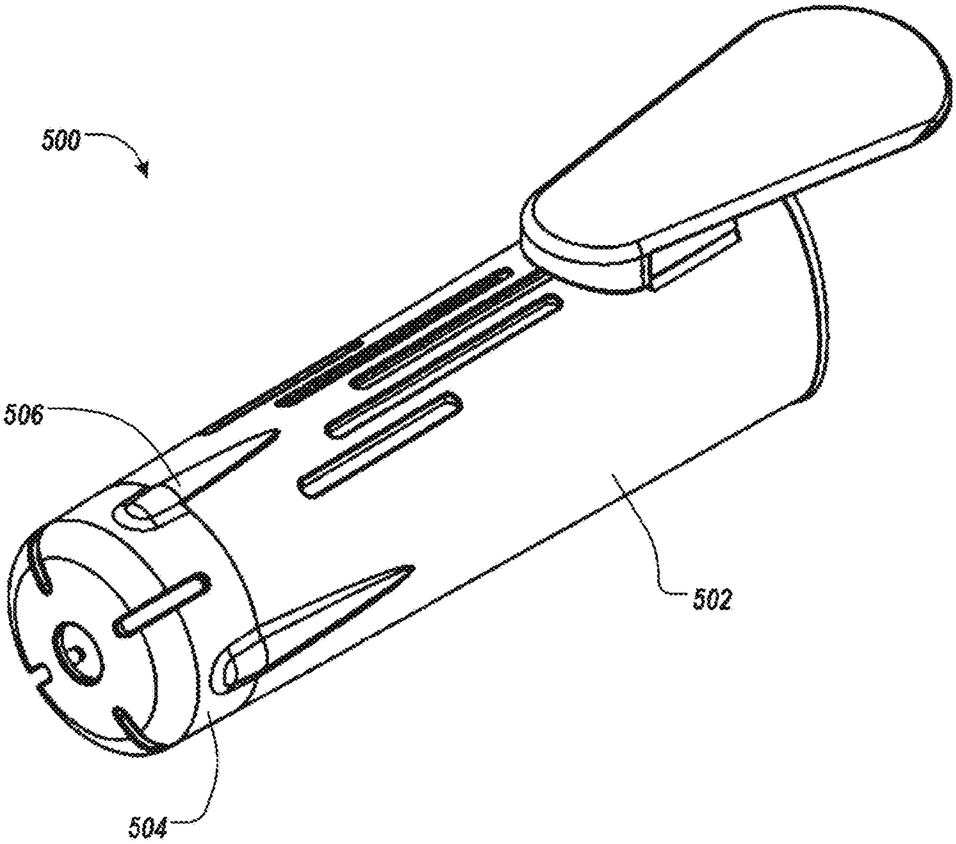
FIGS. 24A and 24B are perspective and side views of another alternative implementation of the enclosure device of FIG. 19.
Figure 24B:
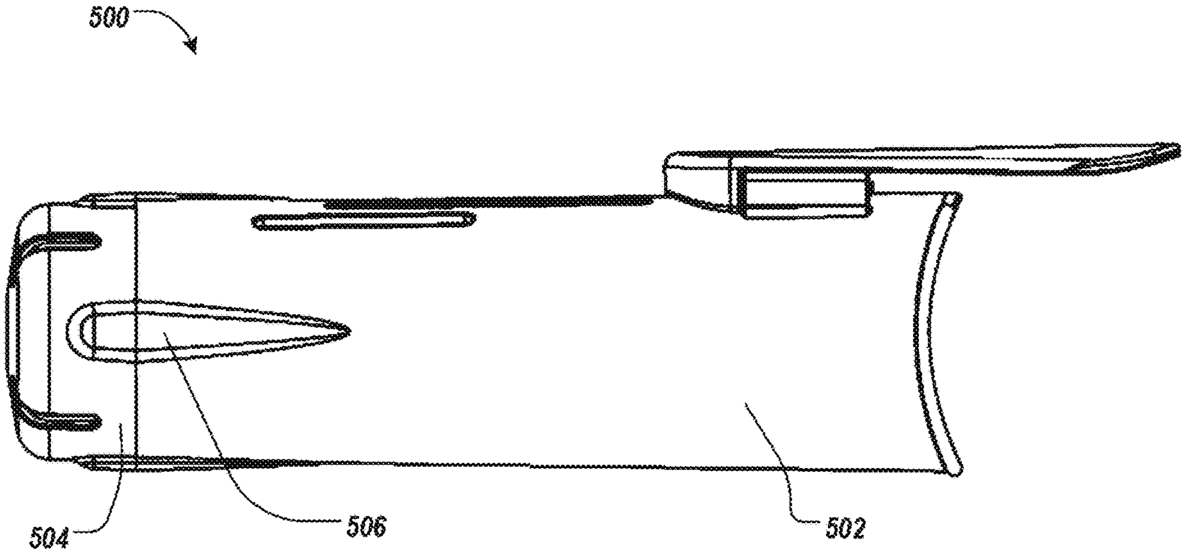

Referring to FIGS. 24A and 24B, an alternative enclosure device 500 includes a tubular portion 502 and an end cap portion 504. Similar to the device 400, the end cap portion 504 can be removably coupled to the tubular portion 502 using snap-fit, interference-fit, screw-fit, or other coupling mechanisms. In the depicted implementation, the device 500 includes a plurality of engagement elements 506 around a circumference of the device that utilize an interference fit between the tubular portion 502 and the end cap portion 504 to hold the two portions engaged to each other. With this setup, it may be possible to disengage the coupling by simply pushing a portion of the end cap portion 504 in a distal direction.

As shown in FIGS. 19-24, the enclosure device 400, 500 can include various ventilation openings that help, for example, promote air and moisture circulation within the device. Additionally, the device 400, 500 can be made from any rigid, semi-rigid, or flexible materials, including combinations thereof.

Figure 25A:
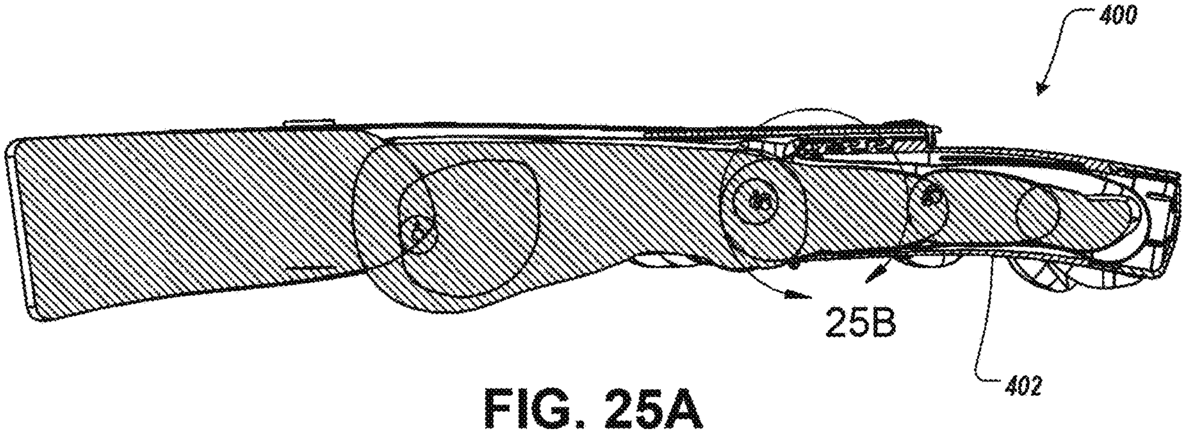
FIGS. 25A and 25B are side cross-sectional views of the enclosure device of FIG. 19 in use.

In use, as illustrated in FIG. 25A, an interface member 420 is placed over the finger and positioned within the tubular portion 402 of the device 400. Similar to the interface member 314, the interface member 420 covers the finger and can include a slippery external surface that facilitates sliding against an interior surface of the tubular portion 402. The interface member 420 may be pre-positioned inside the device 400 prior to insertion of the finger, or alternatively, the interface member 420 may first be placed around the finger prior to insertion.

Figure 25B:
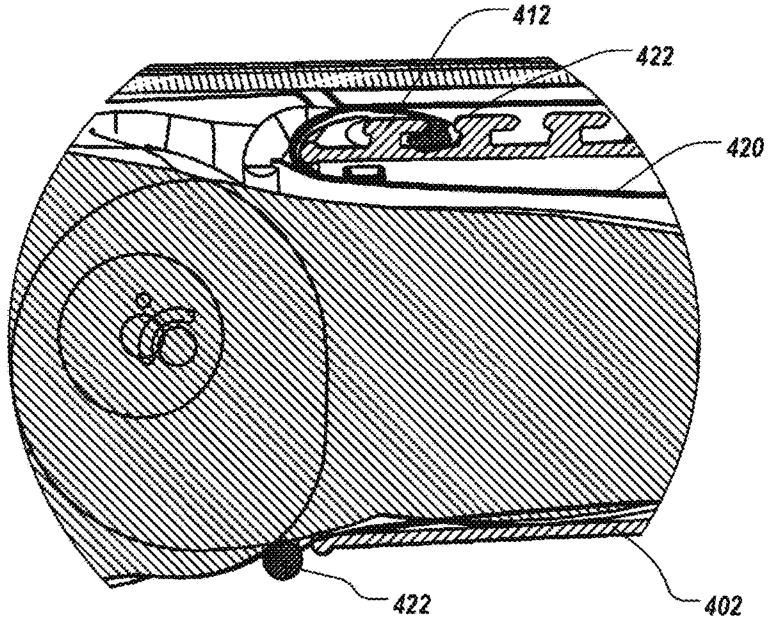

Referring also to FIG. 25B, the interface member 420 can be secured in place by pulling over and latching onto one of the securing hooks 412, Further securing the interface member 420 in this way can help limit the interface member 420 from sliding up the finger during, for example, repeated bending and unbending of the finger. In some implementations, as shown in FIG. 25B, the interface member 420 can include a rolled edge 422 that further limits an open end portion of the interface member 420 from becoming unlatched from the securing hooks 412. By providing a series of the securing hooks 412 along a length of the tubular portion 402, an amount of the interface member 420 that comes in contact with the finger can be adjusted. Alternatively, or additionally, an overall elasticity of the interface member 420 may be adjusted in a similar manner.

Figure 26:
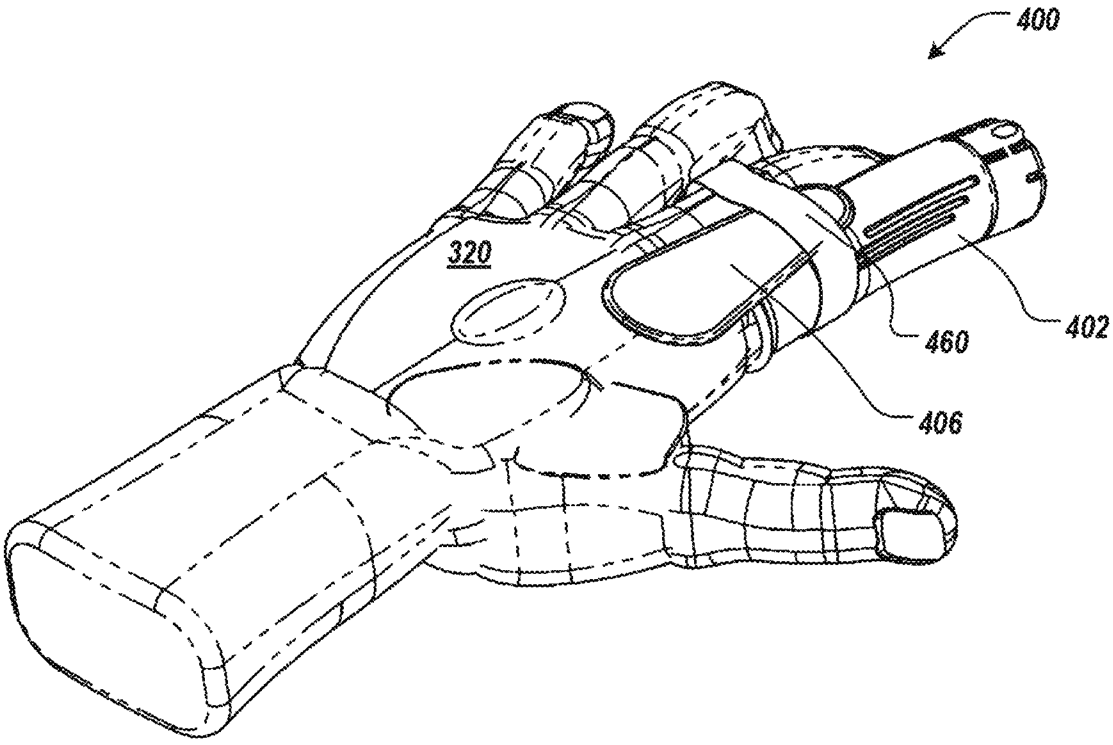
FIG. 26 is a perspective view of the enclosure device of FIG. 19 in use.

FIG. 26 illustrates the device 400 attached to the left hand 320 and enclosing the second (i.e. index) finger. The device 400 can be attached to the hand 320 by securing to an adjacent finger. As shown in FIG. 26, the device 400 is attached to the third (i.e. middle) finger by wrapping an attachment device 460 around the device 400 and the third finger. As a result, the device 400 is not attached to the enclosed protected finger. The attachment device 460 may be a tab, a tape, a strap, a tie, a clip, or a hook-and-loop fastener, just to name a few. The attachment device 460 may be elastic. The attachment device 460 may be wrapped around any one or more of the fingers, including the thumb. In some implementations, the attachment device 460 may be wrapped around the palm or other nearby musculoskeletal structures. While the depicted implementation shows the attachment device 460 being wrapped around both the tubular portion 402 and the knuckle guard 406 of the device 400, the attachment device 460 may similarly be wrapped around only the tubular portion 402 or only the knuckle guard 406.

Figure 27A:
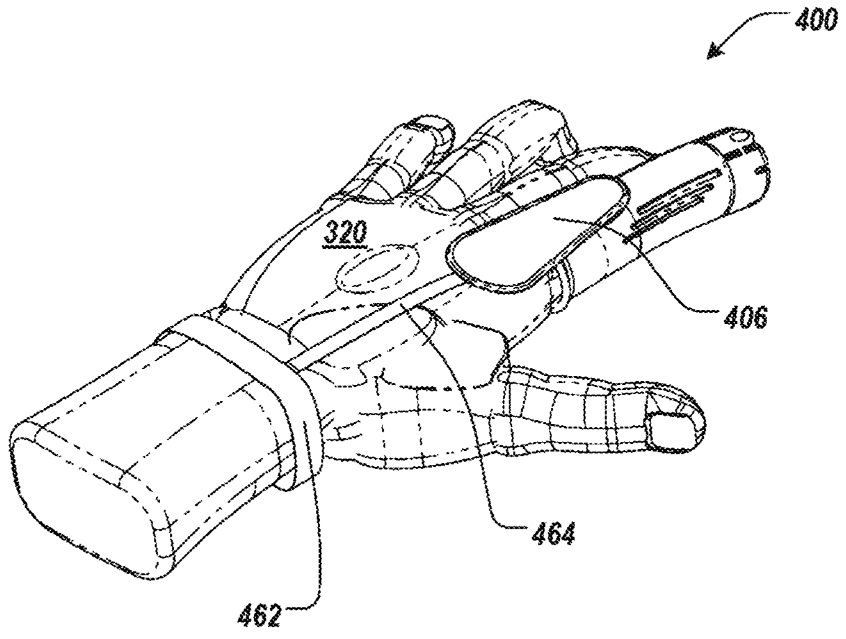
FIGS. 27A and 27B are alternative perspective views of the enclosure device of FIG. 19 in use.
Figure 27B:
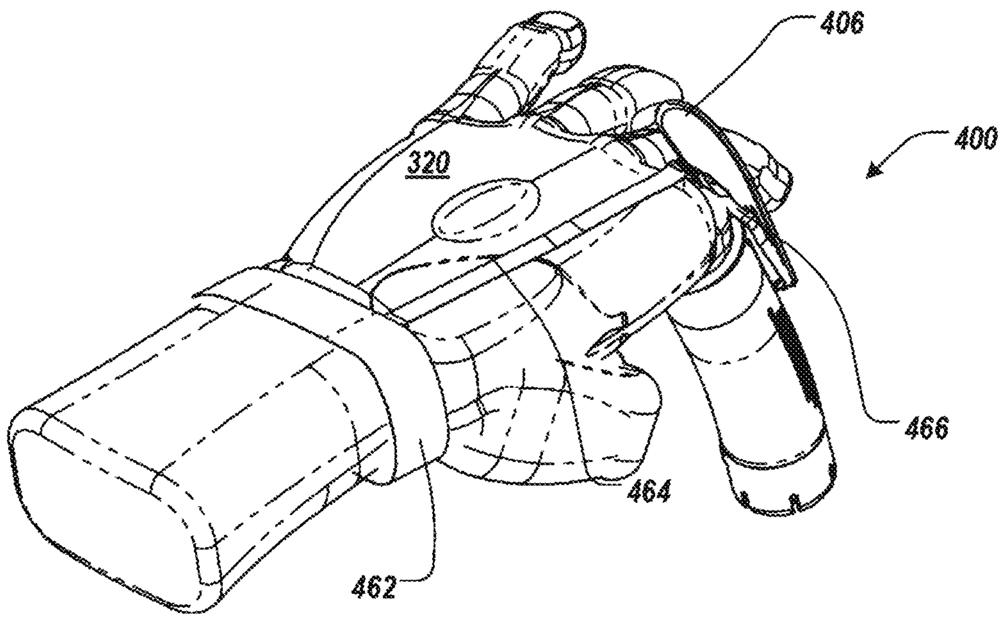

Referring to FIGS. 27A and 27B, the device 400 can be attached to the hand 320 by being secured to other portions of the arm. As shown, the device 400 is attached to a wrist strap 462 via an elastic band 464. The elastic band 464 can include a loop 466 on its distal end that wraps around the knuckle guard 406 to secure the device 400 to the hand 320. In use, as shown in FIG. 27B, the elastic band 464 can stretch as the finger that is enclosed by the device 400 is flexed, thereby ensuring that that device 400 remains attached to the wrist of the hand 320 while still allowing the device 400 to move with the finger and allowing the enclosed finger to move freely inside the tubular portion 402 of the device 400.

A number of implementations have been described, and share many features. For example, the various support shell implementations described above each extends a distance beyond an anticipated range of motion of an injured musculoskeletal structure, or a musculoskeletal structure adjacent thereto, in order to reduce the opportunity for contact with foreign objects. Nevertheless, it will be understood that various modifications may be made without departing from the spirit and scope of the invention.

For example, a low friction interface can be created between a surface of any type of support or brace and the wearer's skin. As one example, a soft, elastomeric knee brace can be provided with a low friction surface facing the wearer's skin in the area of the kneecap, and can be worn with a thin liner, e.g., of fabric, that provides a low coefficient of friction interface where it contacts the low friction surface.

Moreover, in the context of the toe support device discussed above, other areas of the shoe portion 12 can be provided with a sliding surface, in addition to the footbed. For example, if the wearer has an injury to another part of the foot, or if a particular musculoskeletal condition requires additional controlled restraint of motion around the injury site, a sliding surface can be provided on the interior of the shoe upper in the area of that injury.

Additionally, injured musculoskeletal structures that can be supported and/or protected as described above include broken or bruised bones, torn or strained ligaments, torn or bruised cartilage, or torn or strained muscles. Similarly, malformed structures, and diseased structures, such as musculoskeletal structures affected by rheumatory diseases, can be supported and/or protected as described above. Moreover, while mobilization of musculoskeletal structures has been described above with respect to support and/or protection during healing of an injury, the musculoskeletal structures can be mobilized in many situations, which, for the purpose of this disclosure, are considered to be included in the term healing. For example, an injured musculoskeletal structure can be mobilized during support and/or protection thereof while more critical injuries are addressed. Additionally, in situations involving chronic diseases, pain management or other maintenance procedures are considered to be included in the term healing as used herein.

Accordingly, other embodiments are within the scope of the following claims.

What is claimed is:

1. A device for protecting an injured finger or thumb, the device comprising:

a protective shell formed of at least one of a rigid and a semi-rigid material, the protective shell defining an interior cavity and an opening for receiving the injured finger or thumb into the interior cavity; and an attachment device configured to secure the protective shell to one or more musculoskeletal structures of a hand or arm adjacent to the injured finger or thumb, wherein the protective shell is configured to be held in place without being attached directly to the injured finger or thumb, wherein the interior cavity is sized and shaped to provide clearance space around the injured finger or thumb and is configured to allow the injured finger or thumb to move freely within the interior cavity relative to the protective shell and to allow partial or full extension and flexion of the injured finger or thumb within the interior cavity, wherein the protective shell comprises two opposing sidewalls, each oriented generally along a plane defined by an arc of motion of a distal end of the injured finger or thumb between an extended position and a flexed position, wherein distal ends of each respective one of the two opposing sidewalls are configured to extend beyond the distal end of the injured finger or thumb throughout at least a portion of the arc of motion, wherein a volar side of the protective shell comprises a generally semi-cylindrical geometry configured to provide clearance space to accommodate partial or full flexion and extension of the injured finger or thumb, and wherein the protective shell is configured to permit sliding movement of the injured finger or thumb relative to the protective shell during flexion and extension, wherein the protective shell is configured to remain substantially stationary relative to the musculoskeletal structures adjacent to the injured finger or thumb while the injured finger or thumb moves within the interior cavity.

2. The device of claim 1, wherein the protective shell comprises a slippery inner surface configured to reduce friction between the protective shell and the injured finger or thumb.

3. The device of claim 2, wherein the protective shell is configured to provide clearance space between the slippery inner surface and at least one of a bandage, a splint, and an interface member configured to be used with the injured finger or thumb.

4. The device of claim 1, wherein the protective shell comprises one or more ventilation openings.

5. The device of claim 1, wherein the protective shell is configured to provide an interior cavity sized and shaped to provide clearance space around at least one interphalangeal joint of the injured finger or thumb.

6. The device of claim 1, further comprising a dorsal tab comprising at least one of a rigid and a semi-rigid material, wherein the dorsal tab protrudes proximally from a dorsal side of the opening to provide a securing point for the attachment device, and further comprising a supporting portion positioned adjacent to the volar side of the opening, the supporting portion configured to contact an adjacent palm of the hand and to provide a second securing point for the attachment device, wherein the attachment device comprises one or more straps, wraps, bandages, bands, or fasteners configured to secure the protective shell to at least one portion of the adjacent hand or arm proximal to the protective shell.

7. The device of claim 1, wherein the device is configured to be assembled by a user or practitioner from two or more parts.

8. A method for protecting an injured finger or thumb using a device that is not designed to be directly attached to the injured finger or thumb, said method comprising the steps of:

providing a device comprising a protective shell formed of at least one of a rigid and a semi-rigid material;

sizing and shaping the protective shell to form an interior cavity configured to receive the injured finger or thumb and to provide space around the injured finger or thumb within the interior cavity, thus allowing the injured finger or thumb to move freely within the protective shell;

configuring the protective shell to provide an opening for inserting the injured finger or thumb therein;

configuring the protective shell to have two opposing sidewalls, wherein the two opposing sidewalls are each oriented generally parallel to a plane defined by an arc of motion of a distal end of the injured finger or thumb between an extended position and a flexed position, and wherein each respective one of the two opposing sidewalls is configured to extend beyond the distal end of the injured finger or thumb throughout at least a portion of the arc of motion;

configuring the protective shell to provide space within the interior cavity to allow a desired range of extension and flexion of the injured finger or thumb;

configuring the protective shell to be attached to one or more portions of a hand or arm adjacent to the injured finger or thumb;

attaching the protective shell to the one or more portions of the hand or arm adjacent to the injured finger or thumb using one or more attachment devices; and permitting sliding movement of the injured finger or thumb relative to the protective shell during flexion and extension such that the protective shell remains substantially stationary relative to musculoskeletal structures adjacent to the injured finger or thumb while the injured finger or thumb moves within the interior cavity.

9. The method of claim 8, wherein the protective shell comprises a slippery inner surface configured for facing the injured finger or thumb.

10. The method of claim 8, wherein the protective shell is configured to provide clearance space for the injured finger or thumb with at least one of a bandage, a splint, a cast, and an interface member configured to be applied to the injured finger or thumb.

* * * * *